United States Patent
Bukanov et al.

(10) Patent No.: US 12,150,938 B2
(45) Date of Patent: Nov. 26, 2024

(54) BIOMARKER OF POLYCYSTIC KIDNEY DISEASE AND USES THEREOF

(71) Applicant: Genzyme Corporation, Cambridge, MA (US)

(72) Inventors: Nikolai Bukanov, Boston, MA (US); Sarah Moreno, Dudley, MA (US); Timothy E. Weeden, Sturbridge, MA (US)

(73) Assignee: Genzyme Corporation, Cambridge, MA (US)

( * ) Notice: Subject to any disclaimer, the term of this patent is extended or adjusted under 35 U.S.C. 154(b) by 349 days.

(21) Appl. No.: 17/404,701

(22) Filed: Aug. 17, 2021

(65) Prior Publication Data

US 2021/0379031 A1    Dec. 9, 2021

Related U.S. Application Data

(62) Division of application No. 15/775,736, filed as application No. PCT/US2016/062075 on Nov. 15, 2016, now Pat. No. 11,116,755.

(60) Provisional application No. 62/257,089, filed on Nov. 18, 2015.

(51) Int. Cl.
| A61K 31/439 | (2006.01) |
| A61K 31/137 | (2006.01) |
| A61K 31/166 | (2006.01) |
| A61K 45/06 | (2006.01) |
| A61P 13/12 | (2006.01) |
| G01N 33/68 | (2006.01) |

(52) U.S. Cl.
CPC .......... *A61K 31/439* (2013.01); *A61K 31/137* (2013.01); *A61K 31/166* (2013.01); *A61K 45/06* (2013.01); *A61P 13/12* (2018.01); *G01N 33/6893* (2013.01); *G01N 2333/4728* (2013.01); *G01N 2800/347* (2013.01); *G01N 2800/52* (2013.01); *G01N 2800/56* (2013.01)

(58) Field of Classification Search
CPC .. A61K 31/137; A61K 31/166; A61K 31/439; A61K 45/06; A61P 13/12; G01N 2333/4728; G01N 2800/347; G01N 2800/52; G01N 2800/56; G01N 33/6893
See application file for complete search history.

(56) References Cited

U.S. PATENT DOCUMENTS

| | | |
|---|---|---|
| 2001/0025379 A1 | 9/2001 | Wang et al. |
| 2002/0002178 A1 | 1/2002 | Misra |
| 2002/0013328 A1 | 1/2002 | Markwalder et al. |
| 2002/0042412 A1 | 4/2002 | Zaharevitz et al. |
| 2002/0065293 A1 | 5/2002 | Havlicek et al. |
| 2003/0073686 A1 | 4/2003 | Nugiel et al. |
| 2004/0006074 A1 | 1/2004 | Kelley et al. |
| 2004/0048849 A1 | 3/2004 | Prevost et al. |
| 2004/0063715 A1 | 4/2004 | Paruch et al. |
| 2004/0072835 A1 | 4/2004 | Paruch et al. |
| 2004/0073969 A1 | 4/2004 | Inze et al. |
| 2004/0097516 A1 | 5/2004 | Dwyer et al. |
| 2004/0097517 A1 | 5/2004 | Dwyer et al. |
| 2004/0102451 A1 | 5/2004 | Guzi et al. |
| 2004/0106624 A1 | 6/2004 | Guzi et al. |
| 2004/0110775 A1 | 6/2004 | Griffin et al. |
| 2004/0116442 A1 | 6/2004 | Guzi et al. |
| 2004/0198757 A1 | 10/2004 | Newcombe et al. |
| 2004/0209878 A1 | 10/2004 | Guzi et al. |
| 2004/0248905 A1 | 12/2004 | Markwalder et al. |
| 2005/0004007 A1 | 1/2005 | Grant et al. |
| 2005/0130980 A1 | 6/2005 | Paruch et al. |
| 2005/0261353 A1 | 11/2005 | Nugiel et al. |
| 2006/0030555 A1 | 2/2006 | Dwyer et al. |
| 2006/0040958 A1 | 2/2006 | Guzi et al. |
| 2006/0041131 A1 | 2/2006 | Guzi et al. |
| 2006/0106023 A1 | 5/2006 | Guzi et al. |
| 2006/0128725 A1 | 6/2006 | Guzi et al. |
| 2006/0135589 A1 | 6/2006 | Berdino et al. |
| 2006/0173016 A1 | 8/2006 | Guzi et al. |
| 2006/0173017 A1 | 8/2006 | Guzi et al. |
| 2006/0178371 A1 | 8/2006 | Guzi et al. |
| 2007/0259918 A1 | 11/2007 | Orchard et al. |
| 2010/0184110 A1 | 7/2010 | Pugia |
| 2010/0256216 A1 | 10/2010 | Siegel et al. |
| 2011/0166134 A1 | 7/2011 | Ibraghimov-Beskrovnaya et al. |
| 2011/0184021 A1 | 7/2011 | Siegel et al. |
| 2011/0195903 A1 | 8/2011 | Adra |
| 2011/0229895 A1 | 9/2011 | Walz |

(Continued)

FOREIGN PATENT DOCUMENTS

| AU | 2012/318734 | 4/2014 |
| CN | 102018702 | 4/2011 |

(Continued)

OTHER PUBLICATIONS

Abe et al., "Improved Inhibitors of Glucosylceramide Synthase," The Journal of Biochemistry, Feb. 1992, 111:191-196.

(Continued)

*Primary Examiner* — Galina M. Yakovleva

(74) *Attorney, Agent, or Firm* — Fish & Richardson P.C.

(57) ABSTRACT

Provided herein are methods for determining the efficacy of treatment for polycystic kidney disease (PKD) in a patient, diagnosing PKD in a patient, staging PKD in a patient, and monitoring PKD in a patient. These methods include determining a single or multiple levels of AMBP. Also provided are kits that include an antibody specifically binds to AMBP protein and at least one antibody that specifically binds to an additional marker of PKD.

9 Claims, 8 Drawing Sheets

Specification includes a Sequence Listing.

(56) References Cited

U.S. PATENT DOCUMENTS

| | | |
|---|---|---|
| 2012/0322786 A1 | 12/2012 | Siegel et al. |
| 2012/0322787 A1 | 12/2012 | Siegel et al. |
| 2013/0095089 A1 | 4/2013 | Larsen et al. |
| 2013/0137743 A1 | 5/2013 | Liu et al. |
| 2013/0225443 A1 | 8/2013 | Osafune et al. |
| 2013/0225573 A1 | 8/2013 | Ibraghimov-Beskrovnaya et al. |
| 2013/0276513 A1 | 10/2013 | Sharma et al. |
| 2014/0079769 A1 | 3/2014 | Terzi et al. |
| 2017/0227551 A1 | 8/2017 | Beskrovnaya et al. |
| 2018/0338961 A1 | 11/2018 | Bukanov et al. |

FOREIGN PATENT DOCUMENTS

| | | |
|---|---|---|
| CN | 102590491 | 7/2012 |
| EP | 2160478 | 3/2010 |
| EP | 2341344 | 7/2011 |
| JP | 2003-500418 | 1/2003 |
| JP | 2008-507540 | 3/2008 |
| JP | 2010-529458 | 8/2010 |
| JP | 2013-544089 | 12/2013 |
| JP | 2015-527406 | 9/2015 |
| JP | 2015-527870 | 9/2018 |
| WO | WO 2000/071706 | 11/2000 |
| WO | WO 2006/012394 | 2/2006 |
| WO | WO 2010/141862 | 12/2010 |
| WO | WO 2013/052505 | 4/2013 |
| WO | WO 2014/006093 | 1/2014 |
| WO | WO 2014/043068 | 3/2014 |

OTHER PUBLICATIONS

Aerts et al., "Pharmacological Inhibition of Glucosylceramide Synthase Enhances Insulin Sensitivity," Diabetes, May 2007, 56(5):1341-1349.

Alvarez et al., "Comparison of protein, microRNA, and mRNA yields using different methods of urinary exosome isolation for the discovery of kidney disease biomarkers," Kidney International, Nov. 2012, 82:1024-1032.

Anderson et al., "2-Hydroxyestradiol slows progression of experimental polycystic kidney disease," American Journal of Physiology—Renal Physiology, Mar. 2012, 303:F636-F645.

Ashe et al., "Iminosugar-Based Inhibitors of Glucosylceramide Synthase Increase Brain Glycosphingolipids and Survival in a Mouse Model of Sandhoff Disease," PLoS One, Jun. 2011, 6:e21758, 11 pages.

Belibi et al., "Novel targets for the treatment of autosomal dominant polycystic kidney disease," Expert Opinion Investigational Drugs, Feb. 2010, 19:315-328.

Belibi et al., "mTORC1/2 and rapamycin in female Han:SPRD rats with polycystic kidney disease," American Journal of Physiology—Renal Physiology, Jan. 2011, 300:F236-F644.

Bijl et al., "The Glucosylceramide Synthase Inhibitor N-(5-Adamantane-1-yl-methoxy-pentyl)-deoxynojirimycin Induces Sterol Regulatory Element-Binding Protein-Regulated Gene Expression and Cholesterol Synthesis in HepG2 Cells," The Journal of Pharmacology and Experimental Therapeutics, Sep. 2008, 326:849-855.

biocompare.com [online], "Anti-alpha 1 microglobulin/bikunin Antibody Products," retrieved on Jul. 14, 2020, retrieved from URL <https://biocompare.com/pfu/110447/soids/318230/Antibodies/alpha_1_microglobulinbikunin>, 25 pages.

Birenboim et al., "Renal excretion and cyst accumulation of β2microglobul in polycystic kidney disease," Kidney International, Jan. 1987, 31(1):85-92.

Blachly et al., "Emerging Drug Profile: Cyclin-Dependent Kinase Inhibitors," Leukemia & Lymphoma, Jul. 2013, 54:2133-2143.

Bukanov et al., "CDK inhibitors R-roscovitine and S-CR8 effectively block renal and hepatic cystogenesis in an orthologous model of ADPKD," Cell Cycle, Nov. 2012, 11(21):4040-4046.

Cantley et al., "Development of a targeted urine proteome assay for kidney disease," Proteomics Clin. Appl., 2016, vol. 10, pp. 58-74.

Chapin et al., "The cell biology of polycystic kidney disease," Journal of Cell Biology, Nov. 2010, 191:701-710.

Chen et al., "Microfluidic isolation and transcriptome analysis of serum microvesicles," Lab Chip, Feb. 2010, 10:505-511.

Cheruvanky et al., "Rapid isolation of urinary exosomal biomarkers using a nanomembrane ultrafiltration concentrator," Am. J. Physiol. Renal Physiol., Jan. 2007, 292:F1657-F1661.

Chinese Office Action in Patent Application No. 201580053081.4, dated Apr. 2, 2019, 19 pages.

Chinese Office Action in Patent Application No. 201580053081.4, dated Jan. 19, 2018, 14 pages.

Chinese Office Action in Patent Application No. 201580053081.4, dated Oct. 28, 2019, 33 pages.

Chinese Office Action in Patent Application No. 201580053081.4, dated Sep. 29, 2018, 23 pages.

Chinese Office Action in Patent Application No. 201680079045.X, dated Sep. 3, 2020, 12 pages.

Chinese Patent Office Action in Patent Application No. 201580053081.4, dated Apr. 2, 2020, 14 pages.

Cicenas et al., "The CDK inhibitors in cancer research and therapy," J. Cancer Res. Clin. Oncol., Oct. 2011, 138:1409-1418.

Columbian Office Action in Patent Application No. NC2017/0001596, dated Jul. 19, 2018, 23 pages.

Columbian Office Action in Patent Application No. NC2017/0001596, dated Nov. 13, 2018, 23 pages.

Communication in European Patent Application No. 16809582.6, dated Apr. 9, 2019, 3 pages.

Communication in European Patent Application No. 16809582.6, dated Jun. 29, 2018, 3 pages.

European Office Action in Patent Application No. 15757363.5, dated Oct. 23, 2019, 4 pages.

Fischer et al., "Activation of the AKT/mTOR pathway in autosomal recessive polycystic kidney disease," (ARPKD), Nephrology Dialysis Transplantation, Jun. 2009, 24(6):1819-1827.

Flynn et al., "Urinary excretion of beta 2-glycoprotein-1 (apolipoprotein H) and other markers of tubular malfunction in 11 non-tubular," Journal of Clinical Pathology, Jul. 1992, 45(7):561-567.

Galons et al., "Cyclin-dependent kinase inhibitors: a survey of recent patent literature," Expert Opin. Ther. Pat., Mar. 2010, 20:377-404.

Gevers et al., "Rationale and design of the resolve trail; lanreotide as a volume reducing treatment for polycystic livers in patients with autosomal dominant polycystic kidney disease," BMC Nephrology, Dec. 2012, 13(1):1-7.

Geyer et al., "Targeting malaria with specific CDK inhibitors," Biochim. Biophys. Acta, Sep. 2005, 1754(1-2):160-170.

Gonzalez et al., "Large-Scale Proteomics and Phosphoproteomics of Urinary Exosomes," Journal of the American Society of Nephrology, Feb. 2009, 20(2):363-379.

Hogan et al., "Characterization of PKD Protein-Positive Exosome-Like Vesicles," Journal of the American Society of Nephrology, Feb. 2009, 20(2): 278-288.

Hogan et al., "Identification of Biomarkers for PKD1 Using Urinary Exosomes," Journal of the American Society of Nephrology, Jul. 2015, 26(7):1661-1670.

Huang et al., "Glucosylceramide synthase inhibitor PDMP sensitizes chronic myeloid leukemia T315I mutant to Bcr-Abl inhibitor and cooperatively induces glycogen synthase kinase-3-regulated apoptosis," The FASEB Journal, Jun. 2011, 25:3661-3673.

Inokuchi et al., "Effects of D-threo-PDMP, an inhibitor of glucosylceramide synthetase, on expression of cell surface glycolipid antigen and binding to adhesive proteins by B16 melanoma cells," Journal of Cellular Physiology, Dec. 1989, 141:573-583.

Inokuchi et al., "Preparation of the active isomer of 1-phenyl-2-decanoylamino-3-morpholino-1-propanol, inhibitor of murine glucocerebroside synthetase," Journal of Lipid Research, May 1987, 28:565-571.

Japanese Office Action in Patent Application No. 2017-506291, dated Aug. 6, 2019, 11 pages.

Japanese Office Action in Patent Application No. 2018-525768, dated Jan. 5, 2021, 14 pages.

(56) References Cited

OTHER PUBLICATIONS

Jia et al., "Chronic treatment with Lisinopril decreases proliferative and apoptotic pathways in autosomal recessive polycystic kidney disease," Pediatric Nephrology, Jun. 2010, 25(6):1139-46.
Jimbo et al., "Development of a New Inhibitor of Glucosylceramide Synthase," The Journal of Biochemistry, Dec. 2000, 127:485-491.
Koltun et al., "Discovery of a new class of glucosylceramide synthase inhibitors," Bioorganic & Medicinal Chemistry Letters, Nov. 2011, 21(22):6773-6777.
Larsen et al., "Property-based design of a glucosylceramide synthase inhibitor that reduces glucosylceramide in the brain," Journal of Lipid Research, Feb. 2012, 53(2):282-291.
Lee et al., "Improved Inhibitors of Glucosylceramide Synthase," Journal of Biological Chemistry, May 1999, 274(21):14662-14669.
Masoumi et al., "Potential pharmacological interventions in polycystic kidney disease," Drugs, Dec. 2007, 67(17):2495-2510.
Mathivanan et al., "Proteomics Analysis of A33 Immunoaffinity-purifies Exosomes Released from the Human Colon Tumor Cell Line LIM10215 Reveals a Tissue-specific Protein Signature," Molecular and Cellular Proteomics, Feb. 2010, 9(2):197-208.
McEachern et al., "A specific and potent inhibitor of glucosylceramide synthase for substrate inhibition therapy of Gaucher disease," Molecular Genetics and Metabolism, Jul. 2007, 91(3):259-267.
Miura et al., "Synthesis and evaluation of morpholino- and pyrrolidinosphingolipids as inhibitors of glucosylceramide synthase," Bioorganic & Medicinal Chemistry, Sep. 1998, 6(9):1481-1489.
Natoli et al., "Inhibition of glucosylceramide accumulation results in effective blockade of polycystic kidney disease in mouse models," Nature Medicine, Jul. 2010, 16(7):788-792.
Nietupski et al., "Iminosugar-based inhibitors of glucosylceramide synthase prolong survival but paradoxically increase brain glucosylceramide levels in Niemann-Pick C mice," Molecular Genetics and Metabolism, Apr. 2012, 105(4):621-628.
Niino et al., "A small molecule inhibitor of Bcl-2, HA14-1, also inhibits ceramide glucosyltransferase," Biochemical and Biophysical Research Communications, Apr. 2013, 433(2):170-174.
Park et al., "Polycystic kidney disease and therapeutic approaches," BMB Reports, Jun. 2011, 44(6):359-368.
PCT International Preliminary Report on Patentability in International Appln. No. PCT/US2015/043497, dated Feb. 7, 2017, 12 pages.
PCT International Preliminary Report on Patentability in International Appln. No. PCT/US2016/062075, dated May 22, 2018, 6 pages.
PCT International Search Report and Written Opinion in International Appln. No. PCT/US2015/043497, dated Feb. 24, 2016, 19 pages.
PCT International Search Report and Written Opinion in International Appln. No. PCT/US2016/062075, dated Feb. 17, 2017, 10 pages.
Pei et al., "Diagnosis and Screening of Autosomal Dominant Polycystic Kidney Disease," Advances in Chronic Kidney Disease, Mar. 2010, 17(2):140-152.
Pisitkun et al., "Application of systems biology principles to protein biomarker discovery: Urinary exosomal proteome in renal transplantation," Proteomics Clinical Applications, May 2012, 6(5-6):268-278.
Pisitkun et al., "Identification and proteomic profiling of exosomes in human urine," Proceedings of the National Academy of Sciences, Sep. 7, 2004, 101(36): 13368-13373.
Richards et al., "Discovery and Characterization of an Inhibitor of Glucosylceramide Synthase," Journal of Medicinal Chemistry, Apr. 2012, 55(9):4322-4325.
Russian Office Action in Patent Application No. 2017106891, dated Mar. 13, 2019, 11 pages.
Salih et al., "Urinary extracellular vesicles and the kidney: biomarkers and beyond," Am. J. Physiol. Renal Physiol, 2014, vol. 306, pp. F1251-F1259.

Salih et al., "Proteomic analysis of urinary extracellular vesicles in ADPKD patients," Third International Meeting of ISEV 2014, ISEV Meeting, dated Apr. 30, 2014, pp. 06C-251.
Schageman et al., "The Complete Exosome Workflow Solution: From Isolation to Characterization of RNA Cargo," BioMed Research International, Sep. 2013, Article 253957, 16 pages.
Shayman et al., "[38] Inhibitors of glucosylceramide synthase," Methods in Enzymology, 2000, 311:373-387.
Shayman, "Eliglustat Tartrate: Glucosylceramide Synthase Inhibitor Treatment of Type 1 Gaucher Disease," Drugs Future, 2010, 35(8):613-620.
Singapore Written Opinion in Patent Application 11201700290S, dated Oct. 26, 2017, 6 pages.
Singapore Written Opinion in Patent Application No. 112017002905, dated Sep. 28, 2018, 6 pages.
Smith et al., "Development of Polycystic Kidney Disease in Juvenile Cystic Kidney Mice: Insights into Pathogenesis, Ciliary Abnormalities, and Common Features with Human Disease," Journal of the American Society of Nephrology, Oct. 2006, 17(10):2821-2831.
Suzuki et al., "Suppression of invasion and peritoneal carcinomatosis of ovarian cancer cell line by overexpression of bikunin," International Journal of Cancer, Apr. 10, 2003, 104(3):289-302.
Takahashi et al., "A hereditary model of slowly progressive polycystic kidney disease in the mouse," Journal of the American Society of Nephrology, Jan. 1991, 1(7):980-989.
Treiber et al., "The pharmacokinetics and tissue distribution of the glucosylceramide synthase inhibitor miglustat in the rat," Xenobiotica, Mar. 2007, 37(3):298-314.
U.S. Appl. No. 15/501,496, filed Feb. 3, 2017, Oxana Beskrovnaya.
U.S. Appl. No. 17/127,377, filed Dec. 18, 2020, Oxana Beskrovnaya.
Office Action in European Patent Application No. 15757363.5, dated Aug. 23, 2018, 5 pages.
Office Action in European Patent Application No. 15757363.5, dated Jun. 22, 2018, 5 pages.
Office Action in European Patent Application No. 16809582.6, dated Apr. 9, 2019, 3 pages.
Office Action in European Patent Application No. 16809582.6, dated Jun. 29, 2018, 3 pages.
Office Action in U.S. Appl. No. 15/501,496, dated Apr. 8, 2020, 16 pages.
Office Action in U.S. Appl. No. 15/501,496, dated Jan. 2, 2019, 15 pages.
Office Action in U.S. Appl. No. 15/501,496, dated Jun. 21, 2019, 13 pages.
Office Action in U.S. Appl. No. 15/775,736, dated Jul. 20, 2020, 13 pages.
Bukanov et al., "Long-lasting arrest of murine polycystic kidney disease with CDK inhibitor roscovitine," Nature, Nov. 22, 2006, 444:949-952.
Cristol, "How Does ADPKD Progress?," WebMD, Apr. 7, 2020, retrieved on Jan. 29, 2024, retrieved from URL <https://www.webmd.com/a-to-z-guides/adpkd-stages>, 7 pages.
Daveau et al., "Human inter-α-inhibitor family in inflammation: simultaneous synthesis of positive and negative acute-phase proteins," Biochemical Journal, Jun. 1993, 292(2):485-492.
Grewal et al., "Oxalate-inducible AMBP gene and its regulatory mechanism in renal tubular epithelial cells," Biochemical Journal, May 2005, 387(3):609-616.
Guangfu Jia et al., "Chronic treatment with Lisinopril decreases proliferative and apoptotic pathways in autosomal recessive polycystic kidney disease," Pediatric Nephrology, Jun. 2010, 25(6):1139-1146.
Nhs.uk [online], "Treatment: Autosomal dominant polycystic kidney disease," last reviewed Feb. 23, 2023, retrieved on Jan. 29, 2024, retrieved from URL <https://www.nhs.uk/conditions/autosomal-dominant-polycystic-kidney-disease-adpkd/treatment/>, 3 pages.
Salier et al., "Developmentally regulated transcription of the four liver-specific genes for inter-α-inhibitor family in mouse," Biochemical Journal, Nov. 1993, 296(1):85-91.
Salier et al., "The inter-α-inhibitor family: from structure to regulation," Biochemical Journal, Apr. 1996, 315(1):1-9.

BIOMARKER OF POLYCYSTIC KIDNEY DISEASE AND USES THEREOF

CROSS-REFERENCE TO RELATED APPLICATIONS

This application is a divisional of U.S. patent application Ser. No. 15/775,736, filed May 11, 2018, which is a § 371 U.S. National Application of PCT Application No. PCT/US2016/062075, filed on Nov. 15, 2016, which claims priority to U.S. Provisional Patent Application Ser. No. 62/257,089, filed Nov. 18, 2015, the entire contents of this application is herein incorporated by reference.

SEQUENCE LISTING

This application contains a Sequence Listing that has been submitted electronically as an ASCII text file named "Sequence_Listing.txt." The ASCII text file, created on Aug. 17, 2021, is 56 KB in size. The material in the ASCII text file is hereby incorporated by reference in its entirety.

TECHNICAL FIELD

This invention relates to methods of molecular medicine and molecular biology.

BACKGROUND

Polycystic kidney disease (PKD) is a common genetic disorder characterized by the formation of fluid-filled epithelial-lined cysts in the kidneys of patients over time (Park et al., *BMB Reports* 44:359-368, 2011). The cysts in a PKD patient can increase in size and number over the decades, and displace and destroy adjacent renal parenchyma, which can ultimately lead to end-stage renal disease in the patient (Chapin et al., *J. Cell Biol.* 191:701-710, 2010). Multiple mechanisms have been shown to contribute to PKD, including increased proliferation and apoptosis, in addition to loss of differentiation and polarity (Belibi et al., *Expert. Opin. Invest. Drugs* 19:315-328, 2010). Many end-stage PKD patients depend on transplantation or hemodialysis to attenuate renal failure (Park et al., 2011; supra).

There are two types of PKD: autosomal dominant PKD (ADPKD) and autosomal recessive PKD (ARPKD). In the year 2006, about 500,000 people were diagnosed as having PKD in the U.S., with ADPKD affecting about 1 person out of 500 to 1,000 people, and ARPKD affecting about 1 person out of 20,000 to 40,000 people. ADPKD is the most common inherited disorder of the kidneys and accounts for 5% of the end-stage renal disease patients in the U.S. (Pei et al., *Adv. Chronic Kidney Dis.* 17:140-152, 2010).

SUMMARY

The present invention is based, at least in part, on the discovery that levels of α-1-microglobulin/bikunin precursor (AMBP) are elevated in samples including a biological fluid (e.g., a urine sample) or kidney tissue (e.g., a kidney biopsy sample) from patients having PKD, are increased in samples including a biological fluid (e.g., a urine sample) or kidney tissue (e.g., a kidney biopsy sample) from patients with later stages of PKD as compared to the levels in patients having earlier stages of PKD, and are decreased in samples including a biological fluid (e.g., a urine sample) or kidney tissue (e.g., a kidney biopsy sample) from PKD subjects administered a therapeutically effective treatment of PKD. In view of this discovery, provided herein are methods for determining the efficacy of a treatment for PKD in a patient, diagnosing PKD in a patient, staging PKD in a patient, and monitoring PKD in a patient that include determining a level of AMBP.

Provided herein are methods of determining the efficacy of treatment for polycystic kidney disease (PKD) in a patient that include: (a) providing a first sample including a biological fluid obtained from a PKD patient; (b) determining a level of α-1-microglobulin/bikunin precursor (AMBP) in the first sample; (c) administering a PKD treatment to the patient; (d) providing a second sample including a biological fluid from the patient after step (c) and determining a level of AMBP in the second sample; and (e) identifying the administered treatment as effective if the level in the second sample is lower than the level in the first sample. In some embodiments of these methods, the PKD patient has autosomal dominant PKD. In some embodiments of these methods, the PKD patient has autosomal recessive PKD. In some embodiments of these methods, the first and second samples include urine.

In some embodiments of these methods, the PKD treatment includes a glucosyl ceramide synthase (GCS) inhibitor. In some embodiments of these methods, the GCS inhibitor is selected from the group of: (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide; 4-fluoro-1-(4-(4-((2-methoxyethoxy)methyl)phenyl)pyrimidin-2-yl)-N-(3-methylquinuclidin-3-yl)piperidine-4-carboxamide; 4-fluoro-1-(4-(4-((2-methoxyethoxy) methyl)phenyl)pyrimidin-2-yl)-N-(4-methyl-1-azabicyclo[3.2.2]nonan-4-yl)piperidine-4-carboxamide; 4-fluoro-1-(4-(4-(methoxy methyl)phenyl)pyrimidin-2-yl)-N-(3-methylquinuclidin-3-yl)piperidine-4-carboxamide; 4-fluoro-1-(4-(4-(methoxy methyl) phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy) phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; 4-fluoro-1-(4-(4-(2-fluoroethoxy)phenyl) pyrimidin-2-yl)-N-(4-methyl-1-azabicyclo[3.2.2]nonan-4-yl)piperidine-4-carboxamide; quinuclidin-3-yl (2-(4'-fluoro-[1,1'-biphenyl]-3-yl)propan-2-yl)carbamate; and carbamic acid, N-[1-[2-(4-fluorophenyl)-4-thiazolyl]-1-methylethyl]-, (3S)-1-azabicyclo[2.2.2]oct-3-yl ester.

Some embodiments of these methods further include: (0 administering to the patient additional doses of GCS inhibitor if the treatment is identified as being effective. In some embodiments of these methods, the additional doses of GCS inhibitor include (5)-quinuclidin-3-yl(2-(4'-(2-methoxyethoxy)-[1,1'-biphenyl]-4-yl)propan-2-yl)carbamate; 4-fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide; 4-fluoro-1-(4-(4-((2-methoxyethoxy) methyl)phenyl)pyrimidin-2-yl)-N-(3-methylquinuclidin-3-yl)piperidine-4-carboxamide; 4-fluoro-1-(4-(4-((2-methoxyethoxy) methyl)phenyl)pyrimidin-2-yl)-N-(4-methyl-1-azabicyclo [3.2.2]nonan-4-yl) piperidine-4-carboxamide; 4-fluoro-1-(4-(4-(methoxymethyl)phenyl) pyrimidin-2-yl)-N-(3-methylquinuclidin-3-yl) piperidine-4-carboxamide; 4-fluoro-1-(4-(4-(methoxy methyl)phenyl)pyrimidin-2-yl)-N-(4-methyl-1-azabicyclo

[3.2.2]nonan-4-yl) piperidine-4-carboxamide; 4-fluoro-1-(4-(4-(2-methoxyethoxy) phenyl)pyrimidin-2-yl)-N-(3-methylquinuclidin-3-yl)piperidine-4-carboxamide; 4-fluoro-1-(4-(4-(2-methoxyethoxy) phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl)pyrimidin-2-yl)-N-(quinuclidin-3-yl)piperidine-4-carboxamide; 4-fluoro-1-(4-(4-(2-fluoroethoxy)phenyl)pyrimidin-2-yl)-N-(4-methyl-1-azabicyclo[3.2.2]nonan-4-yl)piperidine-4-carboxamide; quinuclidin-3-yl (2-(4'-fluoro-[1,1'-biphenyl]-3-yl)propan-2-yl)carbamate; or carbamic acid, N-[1-[2-(4-fluorophenyl)-4-thiazolyl]-1-methylethyl]-, (3S)-1-azabicyclo[2.2.2]oct-3-yl ester.

In some embodiments of these methods, the PKD treatment includes a CDK inhibitor (e.g., R-roscovitine or S-CR8). Some embodiments of these methods further include: (f) administering to the patient additional doses of CDK inhibitor if the treatment is identified as being effective. In some embodiments of these methods, the additional doses of CDK inhibitor include R-roscovitine or S-CR8.

In some embodiments of these methods, determining the level of AMBP in (b) and (d) include determining the level of AMBP protein. In some embodiments of these methods, (b) and (d) include contacting the sample with an antibody that binds specifically to AMBP protein.

Also provided herein are methods of determining the stage of polycystic kidney disease (PKD) in a patient that include: (a) providing a sample including a biological fluid from a patient suspected of having PKD or identified as having PKD; (b) determining a level of α-1-microglobulin/bikunin precursor (AMBP) in the sample; and (c) determining the stage of PKD in the patient from the level. In some embodiments of these methods, the PKD is autosomal dominant PKD. In some embodiments of these methods, the PKD is autosomal recessive PKD. In some embodiments of these methods, the sample includes urine.

Some embodiments of these methods further include (d) administering a treatment for stage I, stage II, stage III, stage IV, or stage V PKD to a patient identified to have stage I, stage II, stage III, stage IV, or stage V PKD, respectively. Some embodiments of these methods further include: (d) imaging one or both kidney(s) in the patient after (c) to confirm the stage of PKD in the patient.

In some embodiments of these methods, determining the level of AMBP in (b) includes determining the level of AMBP protein. In some embodiments of these methods, (b) includes contacting the sample with an antibody that binds specifically to AMBP protein.

Also provided are methods of determining the stage of polycystic kidney disease (PKD) in a patient that include: (a) providing a sample including kidney tissue from a patient suspected of having PKD or identified as having PKD; (b) determining a level of α-1-microglobulin/bikunin precursor (AMBP) in the sample; and (c) determining the stage of PKD in the patient from the level. In some embodiments of these methods, the PKD is autosomal dominant PKD. In some embodiments of these methods, the PKD is autosomal recessive PKD.

Some embodiments of these methods further include: (d) administering a treatment for stage I, stage II, stage III, stage IV, or stage V PKD to a patient identified to have stage I, stage II, stage III, stage IV, or stage V PKD, respectively. Some embodiments of these methods further include: (d) imaging one or both kidney(s) in the patient after (c) to confirm the stage of PKD in the patient.

In some embodiments of these methods, determining the level of AMBP in (b) includes determining the level of AMBP protein. In some embodiments of these methods, (b) includes contacting the sample with an antibody that binds specifically to AMBP protein.

Also provided are methods of diagnosing polycystic kidney disease (PKD) in a patient that include: (a) providing a sample including a biological fluid from a patient suspected of having PKD; (b) determining a level of α-1-microglobulin/bikunin precursor (AMBP) in the sample; and (c) identifying the patient as having PKD if the level is elevated as compared to a control level. In some embodiments of these methods, the PKD is autosomal dominant PKD. In some embodiments of these methods, the PKD is autosomal recessive PKD. In some embodiments of any of these methods, the sample includes urine.

Some embodiments of these methods further include: (d) administering a PKD treatment to the patient. In some embodiments of these methods, the PKD treatment includes a glucosyl ceramide synthase (GCS) inhibitor. In some embodiments of these methods, the GCS inhibitor is selected from the group of: (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2-methoxyethoxy) methyl) phenyl)pyrimidin-2-yl)-N-(4-methyl-1-azabicyclo[3.2.2]nonan-4-yl)piperidine-4-carboxamide; 4-fluoro-1-(4-(4-((2-methoxyethoxy)methyl)phenyl)pyrimidin-2-yl)-N-(3-methylquinuclidin-3-yl)piperidine-4-carboxamide; 4-fluoro-1-(4-(4-((2-methoxyethoxy) methyl)phenyl)pyrimidin-2-yl)-N-(4-methyl-1-azabicyclo[3.2.2]nonan-4-yl) piperidine-4-carboxamide; 4-fluoro-1-(4-(4-(methoxymethyl)phenyl)pyrimidin-2-yl)-N-(3-methylquinuclidin-3-yl) piperidine-4-carboxamide; 4-fluoro-1-(4-(4-(methoxymethyl) phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy) phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl)pyrimidin-2-yl)-N-(quinuclidin-3-yl)piperidine-4-carboxamide; 4-fluoro-1-(4-(4-(2-fluoroethoxy)phenyl)pyrimidin-2-yl)-N-(4-methyl-1-azabicyclo[3.2.2]nonan-4-yl)piperidine-4-carboxamide; quinuclidin-3-yl (2-(4'-fluoro-[1,1'-biphenyl]-3-yl)propan-2-yl)carbamate; and carbamic acid, N-[1-[2-(4-fluorophenyl)-4-thiazolyl]-1-methylethyl]-, (3S)-1-azabicyclo[2.2.2]oct-3-yl ester. In some embodiments of these methods, the PKD treatment includes a CDK inhibitor (e.g., R-roscovitine or S-CR8).

Some embodiments of these methods further include: (d) imaging one or both kidney(s) in the patient. In some embodiments of these methods, the control level is a threshold level or a level in a healthy subject or a population of healthy subjects.

In some embodiments of these methods, determining the level of AMBP in (b) includes determining the level of AMBP protein. In some embodiments of these methods, (b) includes contacting the sample with an antibody that binds specifically to AMBP protein.

Also provided herein are methods of diagnosing polycystic kidney disease (PKD) in a patient that include: (a) providing a sample including kidney tissue from a patient suspected of having PKD; (b) determining a level of α-1-microglobulin/bikunin precursor (AMBP) in the sample; and (c) identifying the patient as having PKD if the level is elevated as compared to a control level. In some embodiments of these methods, the PKD is autosomal dominant PKD. In some embodiments of these methods, the PKD is autosomal recessive PKD.

Some embodiments of these methods further include: (d) administering a PKD treatment to the patient. In some embodiments of these methods, the PKD treatment includes a glucosyl ceramide synthase (GCS) inhibitor. In some embodiments of these methods, the GCS inhibitor is selected from the group of: (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2-methoxyethoxy) methyl) phenyl)pyrimidin-2-yl)-N-(4-methyl-1-azabicyclo[3.2.2] nonan-4-yl)piperidine-4-carboxamide; 4-fluoro-1-(4-(4-((2-methoxyethoxy)methyl)phenyl)pyrimidin-2-yl)-N-(3-methylquinuclidin-3-yl)piperidine-4-carboxamide; 4-fluoro-1-(4-(4-((2-methoxyethoxy) methyl)phenyl)pyrimidin-2-yl)-N-(4-methyl-1-azabicyclo[3.2.2]nonan-4-yl) piperidine-4-carboxamide; 4-fluoro-1-(4-(4-(methoxymethyl)phenyl)pyrimidin-2-yl)-N-(3-methylquinuclidin-3-yl) piperidine-4-carboxamide; 4-fluoro-1-(4-(4-(methoxymethyl) phenyl)pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy) phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; 4-fluoro-1-(4-(4-(2-fluoroethoxy)phenyl) pyrimidin-2-yl)-N-(4-methyl-1-azabicyclo[3.2.2]nonan-4-yl)piperidine-4-carboxamide; quinuclidin-3-yl (2-(4'-fluoro-[1,1'-biphenyl]-3-yl)propan-2-yl)carbamate; and carbamic acid, N-[1-[2-(4-fluorophenyl)-4-thiazolyl]-1-methylethyl]-, (3S)-1-azabicyclo[2.2.2]oct-3-yl ester. In some embodiments of these methods, the PKD treatment includes a CDK inhibitor (e.g., R-roscovitine or S-CR8).

Some embodiments of these methods further include: (d) imaging one or both kidney(s) in the patient. In some embodiments of these methods, the control level is a threshold level or a level in a healthy subject or a population of healthy subjects.

In some embodiments of these methods, determining the level of AMBP in (b) includes determining the level of AMBP protein. In some embodiments of these methods, (b) includes contacting the sample with an antibody that binds specifically to AMBP protein. Also provided herein are methods of monitoring a polycystic kidney disease (PKD) patient that include: (a) providing a first sample including a biological fluid obtained from a PKD patient; (b) determining a level of α-1-microglobulin/bikunin precursor (AMBP) in the first sample; (c) providing a second sample including a biological fluid from the patient after step (b) and determining a level of AMBP in the second sample; and (d) identifying the patient as having improving or static PKD if the level in the second sample is not higher than the level in the first sample. In some embodiments of these methods, the PKD patient has autosomal dominant PKD. In some embodiments of these methods, the PKD patient has autosomal recessive PKD. In some embodiments of these methods, the first and second samples include urine.

Some embodiments of these methods further include: (e) administering the same treatment to a patient identified as having improving or static PKD. In some embodiments of these methods, determining the level of AMBP in (b) and (c) include determining the level of AMBP protein. In some embodiments of these methods, (b) and (c) include contacting the sample with an antibody that binds specifically to AMBP protein.

Also provided are kits comprising, consisting, or consisting essentially of: an antibody that specifically binds to α-1-microglobulin/bikunin precursor (AMBP) protein; and an antibody that specifically binds to an additional protein marker of polycystic kidney disease.

As used herein, the word "a" before a noun represents one or more of the particular noun. For example, the phrase "a marker" represents "one or more markers."

The term "patient" means a vertebrate, including any member of the class mammalia, including humans, domestic and farm animals, and zoo, sports or pet animals, such as mouse, rabbit, pig, sheep, goat, cattle, horse (e.g., race horse), and higher primates. In preferred embodiments, the patient is a human.

The term "biological fluid" means any fluid obtained from a mammalian patient (e.g., blood, plasma, serum, or other blood fractions, lymph, urine, cerebrospinal fluid, ascites, saliva, breast milk, tears, vaginal discharge, amniotic fluid, lavage, semen, glandular secretions, exudate, and contents of cysts or feces). In preferred embodiments, the biological fluid is urine, blood, serum, or plasma.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
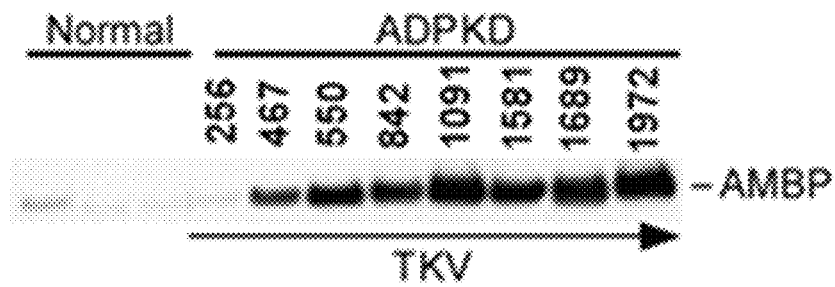
FIG. 1 is an immunoblot showing the level of AMBP protein in urine from two healthy patients (left three lanes; normal) and the level of AMBP protein in urine from ADPKD patients having total kidney volumes ranging from 256 mL to 1972 mL.

Provided herein are methods for determining the efficacy of treatment for PKD (e.g., ADPKD or ARPKD) in a patient, diagnosing PKD in a patient, staging PKD in a patient, and monitoring PKD in a patient that include determining a single or multiple levels of AMBP. Also provided are kits comprising: an antibody that specifically binds to AMBP, and an antibody that specifically binds to an additional protein marker of PKD (e.g., any of the additional protein markers of PKD described herein or known in the art). Non-limiting aspects of these methods are described below. As can be appreciated in the art, the various aspects described below can be used in any combination without limitation.

Polycystic Kidney Disease

The methods described herein can further include a step of identifying or diagnosing a patient as having PKD. Non-limiting examples of diagnosing a patient as having PKD are provided herein and are described below.

In other examples, a patient is identified as having PKD based on the observation or assessment of one or more symptoms of the following symptoms in a patient: high blood pressure, back or side pain, headache, increased size of abdomen, presence of blood in urine, frequent urination, kidney stones, kidney failure, urinary tract or kidney infections, cysts on the kidney, cysts on the liver, pancreatic cysts, mitral valve prolapse, aneurysms, nausea, vomiting, left ventricular hypertrophy, hernia, diverticulitis, fatigue, poor appetite, weight loss, trouble concentrating, dry/itchy skin, muscle cramps, swelling in feet and ankles, mild to moderate depression, and bubbly urine. PKD can also be diagnosed in a subject by performing a genetic test (see, e.g., PKD1 genetic diagnostic tests from a variety of vendors including Athena Diagnostics (Worcester, MA) and CGC Genetics (Porto, Portugal); PKD2 genetic diagnostic tests from a variety of vendors including Centrogene AG (Germany), PreventionGenetics (Marshfield, WI), GCG Genetics (Portugal), and InVitae Corporation (San Francisco, CA); and PKHD1 genetic diagnostic tests are available from a variety of vendors including Centrogene AG (Germany), Prevention Genetics (Marshfield, WI), Counsyl (San Francisco, CA), and Invitae (San Francisco, CA)). The detection of mutations or deletions of the PKD1 and/or PKD2 genes can be used to diagnose ADPKD, and the detection of mutations or deletions in PKHD1 can be used to diagnose ARPKD.

PKD (e.g., ADPKD and ARPKD) can be diagnosed by performing imaging studies. For example, ultrasound, computerized tomography (CT), and magnetic resonance imaging (MRI) can be used to look for cysts on the kidney(s) and to determine the total kidney volume (TKV) or height-adjusted total kidney volume (htTKV). For example, the detection of at least two cysts (e.g., at least three, four, five, or six cysts) on each kidney by age 30 in a patient (e.g., a patient with a family history of the disease) can confirm the diagnosis of PKD. The detection of a multicystic dysplastic kidney(s) in a fetus (e.g., a fetus that is greater than 14 weeks of gestation) can be used to diagnose ARPKD. In addition, the amniotic fluid from a fetus can be used to detect a mutation or deletion in PKHD1 (e.g., using any of the genetic diagnostic tests for PKHD1 described herein or known in the art).

PKD can also be diagnosed or identified in a subject, in part, by determining a patient's kidney function. For example, PKD can be diagnosed and identified in part by measuring one or more of a patient's creatinine level (e.g., a level of creatinine greater than 1.3 mg/dL indicating that the patient has PKD), glomerular filtration rate (e.g., a rate that is below 80 mL/minutes indicates that the patient has PKD), and blood urea nitrogen (e.g., a blood urea nitrogen level of greater than 20 mg/dL).

The PKD patients described herein can be diagnosed or identified using any of the methods described or provided herein, or any methods known in the art. The PKD patient can be in utero (e.g., a fetus with a gestational age greater than 14 weeks, 15 weeks, 17 weeks, 20 weeks, 25 weeks, 30 weeks, or 35 weeks), an infant, an adolescent (between 13 and 18 years old (e.g., between 13 and 15 years old or between 15 and 18 years old)), or an adult (greater than 18 years old (e.g., greater than 20, 22, 24, 26, 28, 30, 32, 34, 36, 38, 40, 45, 50, 55, 60, 65, 70, 75, 80, 85, 90, or 95 years old)). The PKD patient can be a female (e.g., a pregnant female) or can be a male. The PKD patient may already be receiving a treatment for PKD. In other examples, the PKD patient may not have received a treatment for a PKD. In additional examples, the PKD patient may have received a previous treatment for PKD and the previous treatment was therapeutically unsuccessful (e.g., lead to the development of negative adverse side effects, did not reduce the rate of development and/or growth of cysts, and/or did not reduce the rate of loss in the function of the patient's kidney(s)). The PKD patient may be a participant in a clinical study.

PKD Treatments

Some examples of a treatment for PKD is the administration of one or more glucosylceramide synthase (GCS) inhibitors. Non-limiting examples of GSC inhibitors are described in Lee et al. (*J. Biol. Chem.* 274:14662-14669, 1999), Shayman et al. (*Methods Enzymol.* 311:373-387, 2000), Huang et al. (*FASEB J.* 25:3661-3673, 2011), Kolton et al. (*Bioorg. Med. Chem. Lett.* 21:6773-6777, 2011), Larsen et al. (*J. Lipid Res.* 53:282-291, 2012), Niino et al. (*Biochem. Biophys. Res. Comm.* 433:170-174, 2013), Richards et al. (*J. Med. Chem.* 55:4322-4325, 2012), Nietupski et al. (*Mol. Genet. Metab.* 105:621-628, 2012), Ashe et al. (*PLoS One* 6:e21758, 2011), Shayman (Drugs Future 35:613-620, 2010), Bijl et al. (*J. Pharmacol. Exp. Ther.* 326:849-855, 2008), Treiber et al. (*Xenobiotica* 37:298-314, 2007), McEachern et al. (*Mol. Genet. Metab.* 91:259-267, 2007), Wennekes et al. (*Diabetes* 56:1341-1349, 2007), Jimbo et al. (*J. Biochem.* 127:485-291, 2000), Miura et al. (*Bioorg. Med. Chem.* 6:1481-1489, 1998), Abe et al. (*J. Biochem.* 111:191-196, 1992), Inokuchi et al. (*J. Cell Physiol.* 141:573-583, 1989), and Inokuchi et al. (*J. Lipid Res.* 28:565-571, 1987). Additional examples of GCS inhibitors are described in U.S. Patent Application Publication Nos. 2013/0225573, 2013/0137743, 2013/0095089, 2012/0322787, 2012/0322786, 2011/0184021, 2011/0166134, 2010/0256216, and 2007/0259918 (each of which is hereby incorporated by reference).

Additional examples of GCS inhibitors are described in WO 14/043068 (incorporated herein by reference). For example, a GCS inhibitor can have a structure represented by Formula I below.

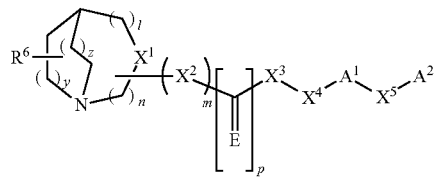

I wherein:
n is 1, 2, or 3;
m is 0 or 1;
p is 0 or 1;
t is 0, 1, or 2;
E is S, O, NH, NOH, $NNO_2$, NCN, NR, NOR or $NSO_2R$;
$X^1$ is $CR^1$ when m is 1 or N when m is 0;
$X^2$ is O, —NH, —$CH_2$, $SO_2$, NH—$SO_2$, $CH(C_1-C_6)$ alkyl or —$NR^2$; $X^3$ is a direct bond, O, —NH, —$CH_2$—, CO, —$CH(C_1-C_6)$ alkyl, $SO_2NH$, —CO—NH—, or $NR^3$;
$X^4$ is a direct bond, $CR^4R^5$, $CH_2CR^4R^5$ or $CH_2$—$(C_1-C_6)$ alkyl-$CR^4R^5$;
$X^5$ is a direct bond, O, S, $SO_2$, $CR^4R^5$, $(C_1-C_6)$alkyl, $(C_1-C_6)$alkyloxy, —O—$(C_1-C_6)$alkyl, $(C_1-C_6)$alkenyl, $(C_1-C_6)$alkenyloxy, —$R^7$—$(C_3-C_{10})$cycloalkyl, $(C_3-C_{10})$cycloalkyl-$R^7$—, —$R^7$—$(C_6-C_{12})$aryl, $(C_6-C_{12})$aryl-$R^7$—, —$R^7$—$(C_2-C_9)$heteroaryl, $(C_2-C_9)$heteroaryl-$R^7$—, —$R^7$—$(C_2-C_9)$heterocycloalkyl, and $(C_2-C_9)$heterocycloalkyl-$R^7$—, wherein $R^7$ is a direct bond, O, S, $SO_2$, $CR^4R^5$, $(C_1-C_6)$alkyl, $(C_1-C_6)$alkyloxy, —O—$(C_1-C_6)$alkyl, $(C_1-C_6)$alkenyl, $(C_1-C_6)$alkenyloxy; and further wherein when $X^5$ is defined as —$R^7$—$(C_3-C_{10})$cycloalkyl, $(C_3-C_{10})$cycloalkyl-$R^7$—, —$R^7$—$(C_6-C_{12})$aryl, $(C_6-C_{12})$aryl-$R^7$—, —$R^7$—$(C^2-C^9)$heteroaryl, $(C_2-C_9)$heteroaryl-$R^7$—, —$R^7$—$(C_2-C_9)$ heterocycloalkyl, and $(C_2-C_9)$heterocycloalkyl-$R^7$—, wherein the $(C_3-C_{10})$cycloalkyl, $(C_6-C_{12})$ aryl, $(C_2-C_9)$heteroaryl, $(C_2-C_9)$ heterocycloalkyl groups are optionally substituted by one or more substituents selected from the group consisting of halo, $(C_1-C_6)$ alkyl, $(C_1-C_6)$ alkylenyl, amino, $(C_1-C_6)$ alkylamino, $(C_1-C_6)$dialkylamino, $(C_1-C_6)$alkoxy, $O(C_3-C_6$ cycloalkyl), $(C_3-C_6)$ cycloalkoxy, nitro, CN, OH, $(C_1-C_6)$ alkyloxy, $(C_3-C_6)$ cycloalkyl, $(C_1-C_6)$ alkoxycarbonyl, $(C_1-C_6)$ alkylcarbonyl, $(C_1-C_6)$halo alkyl, $(C_2-C_9)$heterocycloalkyl, $R^8R^9N$—CO— wherein $R^8$ and $R^9$ are each independently selected from the group consisting of hydrogen and $(C^1-C^6)$alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$alkylsulfonyl optionally substituted by one or two groups selected from $(C_1-C_6)$ alkoxy and $(C_3-C_{10})$cycloalkyl;
$(C_1-C_6)$alkyl substituted by one to four substituents selected from the group consisting of halo, hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy; and
$(C_1-C_6)$alkyloxy substituted by one to four substituents selected from the group consisting of halo, hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

R is $(C_6\text{-}C_{12})$aryl, $(C_2\text{-}C_9)$heteroaryl, $(C_1\text{-}C_6)$alkyl, $(C_2\text{-}C_9)$heteroaryl$(C_1\text{-}C_6)$alkyl;

$R^1$ is H, CN, $(C_1\text{-}C_6)$alkylcarbonyl, or $(C_1\text{-}C_6)$alkyl;

$R^2$ and $R^3$ are each independently —H, $(C_1\text{-}C_6)$alkyl optionally substituted by one or more substituents selected from the group consisting of halogen, $(C_1\text{-}C_6)$alkyl, $(C_6\text{-}C_{12})$aryl, $(C_2\text{-}C_9)$heteroaryl, $(C_1\text{-}C_6)$alkyl$(C_6\text{-}C_{12})$aryl, halo$(C_6\text{-}C_{12})$aryl, and halo$(C_2\text{-}C_9)$heteroaryl, or optionally when $X^2$ is —$NR^2$ and $X^3$ is —$NR^3$, $R^2$ and $R^3$ may be taken together with the nitrogen atoms to which they are attached form a non-aromatic heterocyclic ring optionally substituted by with one or more substituents selected from halogen, $(C_1\text{-}C_6)$alkyl, $(C_6\text{-}C_{12})$aryl, $(C_2\text{-}C_9)$heteroaryl, $(C_1\text{-}C_6)$alkyl$(C_6\text{-}C_{12})$aryl, halo$(C_6\text{-}C_{12})$aryl, and halo $(C_2\text{-}C_9)$heteroaryl;

$R^4$ and $R^5$ are independently selected from H, $(C_1\text{-}C_6)$ alkyl, or taken together with the carbon to which they are attached to form a spiro $(C_3\text{-}C_{10})$cycloalkyl ring or spiro $(C_3\text{-}C_{10})$cycloalkoxy ring;

$R^6$ is —H, halogen, —CN, $(C_6\text{-}C_{12})$aryl, $(C_6\text{-}C_{12})$aryloxy, $(C_1\text{-}C_6)$alkyloxy; $(C_1\text{-}C_6)$alkyl optionally substituted by one to four halo or $(C_1\text{-}C_6)$alkyl;

$A^1$ is $(C_2\text{-}C_6)$alkynyl; $(C_3\text{-}C_{10})$cycloalkyl, $(C_6\text{-}C_{12})$aryl, $(C_2\text{-}C_9)$heteroaryl, $(C_2\text{-}C_9)$heterocycloalkyl or benzo$(C_2\text{-}C_9)$heterocycloalkyl wherein $A^1$ is optionally substituted with one or more substituents selected from the group consisting of halo, $(C_1\text{-}C_6)$alkyl optionally substituted by one to three halo; $(C_1\text{-}C_6)$alkenyl, amino, $(C_1\text{-}C_6)$alkylamino, $(C_1\text{-}C_6)$ dialkylamino, $(C_1\text{-}C_6)$ alkoxy, nitro, CN, —OH, $(C_1\text{-}C_6)$alkyloxy optionally substituted by one to three halo; $(C_1\text{-}C_6)$alkoxycarbonyl, and $(C_1\text{-}C_6)$ alkylcarbonyl;

$A^2$ is H, $(C_3\text{-}C_{10})$cycloalkyl, $(C_6\text{-}C_{12})$aryl, $(C_2\text{-}C_9)$heteroaryl, $(C_2\text{-}C_9)$heterocycloalkyl or benzo$(C_2\text{-}C_9)$heterocycloalkyl wherein $A^2$ is optionally substituted with one or more substituents selected from the group consisting of halo, $(C_1\text{-}C_6)$alkyl, $(C_1\text{-}C_6)$alkylenyl, amino, $(C_1\text{-}C_6)$ alkylamino, $(C_1\text{-}C_6)$dialkylamino, $(C_1\text{-}C_6)$ alkoxy, O($C_3\text{-}C_6$ cycloalkyl), $(C_3\text{-}C_6)$ cycloalkoxy, nitro, CN, OH, $(C_1\text{-}C_6)$alkyloxy, $(C_3\text{-}C_6)$ cycloalkyl, $(C_1\text{-}C_6)$alkoxycarbonyl, $(C_1\text{-}C_6)$ alkylcarbonyl, $(C_1\text{-}C_6)$ halo alkyl, $(C_2\text{-}C_9)$heterocycloalkyl, $R^8R^9N$—CO—, wherein $R^8$ and $R^9$ are each independently selected from the group consisting of hydrogen and $(C_1\text{-}C_6)$alkyl or R8 and R9 can be taken together with the nitrogen to which they are attached to form a $(C_2\text{-}C_9)$heterocycloalkyl or $(C_2\text{-}C_9)$heterocycloalkyl group optionally substituted by one to three halo groups, $(C_1\text{-}C_6)$alkylsulfonyl optionally substituted by one or two groups selected from $(C_1\text{-}C_6)$alkoxy and $(C_3\text{-}C_{10})$cycloalkyl;

$(C_1\text{-}C_6)$alkyl substituted by one to four substituents selected from the group consisting of halo, hydroxy, cyano, $(C_1\text{-}C_6)$alkoxy, $(C_1\text{-}C_6)$alkoxy$(C_1\text{-}C_6)$alkoxy, $(C_2\text{-}C_9)$heterocycloalkyl, $(C_2\text{-}C_9)$heteroaryl optionally substituted by $(C_1\text{-}C_6)$alkoxy; or $(C_3\text{-}C_{10})$cycloalkoxy optionally substituted by $(C_1\text{-}C_6)$alkoxy; and $(C_1\text{-}C_6)$alkyloxy substituted by one to four substituents selected from the group consisting of halo, hydroxy, cyano, $(C_1\text{-}C_6)$alkoxy, $(C_1\text{-}C_6)$alkoxy$(C_1\text{-}C_6)$alkoxy, $(C_2\text{-}C_9)$heterocycloalkyl, $(C_2\text{-}C_9)$heteroaryl optionally substituted by $(C_1\text{-}C_6)$alkoxy; or $(C_3\text{-}C_{10})$cycloalkoxy optionally substituted by $(C_1\text{-}C_6)$alkoxy;

with the proviso that the sum of n+t+Y+z is not greater than 6;

with the proviso that when p is 0; $X^2$ is NH—$SO^2$ and $X^3$ is NH;

with the proviso that when n is 1; t is O; y is 1; z is 1; $X^2$ is NH; E is O; $X^3$ is NH; $A^2$ is H and $X^5$ is a direct bond; $A^1$ is not unsubstituted phenyl, halophenyl or isopropenyl phenyl;

with the proviso that when n is 1; t is O; y is 1; z is 1; $X^2$ is O; E is O; $X^3$ is NH; $A^1$ is $(C^6\text{—}C^2)$aryl and $X^5$ is a direct bond; $A^2$ is H and $R^4$ is H then $R^5$ is not cyclohexyl; and with the proviso that when $X^3$ is O, —NH, —$CH_2$—, CO, —CH($C_1\text{-}C_6$) alkyl, $SO_2NH$, —CO—NH— or —$NR^3$; and $X^4$ is $CR^4R^5$, $CH_2CR^4R^5$ or $CH_2$—$(C_1\text{-}C_6)$ alkyl-$CR^4R^5$; then $A^2$ must be $(C_3\text{-}C_{10})$cycloalkyl, $(C_6\text{-}C_{12})$aryl, $(C_2\text{-}C_9)$heteroaryl, $(C_2\text{-}C_9)$heterocycloalkyl or benzo$(C_2\text{-}C_9)$heterocycloalkyl substituted with one or more substituents selected from the group consisting of $(C_2\text{-}C_9)$heterocycloalkyl, $R^8R^9N$—CO— wherein $R^8$ and $R^9$ are each independently selected from the group consisting of hydrogen and $(C_1\text{-}C_6)$ alkyl or $R^8$ and $R^9$ can be taken together with the nitrogen to which they are attached to form a $(C_2\text{-}C_9)$heterocycloalkyl or $(C_2\text{-}C_9)$heterocycloalkyl group optionally substituted by one to three halo groups, $(C_1\text{-}C_6)$alkylsulfonyl optionally substituted by one or two groups selected from $(C_1\text{-}C_6)$ alkoxy and $(C_3\text{-}C_{10})$cycloalkyl;

$(C_1\text{-}C_6)$alkyl substituted by one to four substituents selected from the group consisting of hydroxy, cyano, $(C_1\text{-}C_6)$alkoxy, $(C_1\text{-}C_6)$alkoxy$(C_1\text{-}C_6)$alkoxy, $(C_2\text{-}C_9)$heterocycloalkyl, $(C_2\text{-}C_9)$heteroaryl optionally substituted by $(C_1\text{-}C_6)$alkoxy; or $(C_3\text{-}C_{10})$cycloalkoxy optionally substituted by $(C_1\text{-}C_6)$alkoxy; or $(C_1\text{-}C_6)$alkyloxy substituted by one to four substituents selected from the group consisting of hydroxy, cyano, $(C_1\text{-}C_6)$alkoxy, $(C_1\text{-}C_6)$alkoxy$(C_1\text{-}C_6)$alkoxy, $(C_2\text{-}C_9)$heterocycloalkyl, $(C_2\text{-}C_9)$heteroaryl optionally substituted by $(C_1\text{-}C_6)$alkoxy; or $(C_3\text{-}C_{10})$cycloalkoxy optionally substituted by $(C_1\text{-}C_6)$alkoxy.

Additional exemplary GCS inhibitors include:

1-azabicyclo[2.2.2]oct-3-yl [2-(2,4'-difluorobiphenyl-4-yl)propan-2-yl]carbamate;

15 1-azabicyclo[2.2.2]oct-3-yl {2-[4-(1,3-benzothiazol-6-yl)phenyl]propan-2-yl}carbamate;

1-azabicyclo[3.2.2]non-4-yl {1-[5-(4-fluorophenyl)pyridin-2-yl]cyclopropyl}carbamate;

1-azabicyclo[2.2.2]oct-3-yl {1-[3-(4-fluorophenoxy)phenyl]cyclopropyl}carbamate;

1-azabicyclo[2.2.2]oct-3-yl {1-[4-(1,3-benzothiazol-5-yl)phenyl]cyclopropyl}carbamate;

1-azabicyclo[2.2.2]oct-3-yl [1-(4'-fluoro-3'-methoxybiphenyl-4-yl)cyclopropyl]carbamate;

1-azabicyclo[2.2.2]oct-3-yl [3-(4'-fluorobiphenyl-4-yl)oxetan-3-yl]carbamate;

1-azabicyclo[2.2.2]oct-3-yl {1-[6-(4-fluorophenoxy)pyridin-2-yl]cyclopropyl}carbamate;

1-azabicyclo[2.2.2]oct-3-yl [3-(4'-fluorobiphenyl-4-yl)pentan-3-yl]carbamate;

1-azabicyclo[2.2.2]oct-3-yl {2-[2-(4-fluorophenyl)-2H-indazol-6-yl]propan-2 yl}carbamate;

1-azabicyclo[2.2.2]oct-3-yl {2-[2-(1H-pyrrol-1-yl)pyridin-4-yl]propan-2-yl}carbamate;

1-(3-ethyl-1-azabicyclo[2.2.2]oct-3-yl)-3-[1-(4'-fluorobiphenyl-4-yl)cyclopropyl]urea;

N-(1-azabicyclo[2.2.2]oct-3-yl)-N'-[1-(4'-fluorobiphenyl-4yl)cyclopropyl]ethanediamide;

1-azabicyclo[2.2.2]oct-3-yl (1-{4[(4,4difluorocyclohexyl)oxy]phenyl}cyclopropyl) carbamate;

1-(4-methyl-1-azabicyclo[3.2.2]non-4-yl)-3-[1-(5-phenylpyridin-2-yl)cyclopropyl]urea;

1-[1-(4'-fluorobiphenyl-4-yl)cyclopropyl]-I-methyl-3-(3-methyl-1-azabicyclo[2.2.2]oct-3-yl)urea;

1-[1-(4'-fluorobiphenyl-4-yl)cyclopropyl]-I-methyl-3-(3-methyl-1-azabicyclo[2.2.2]oct-3-yl)urea;

1-{2-[4'-(2-methoxyethoxy)biphenyl-4-yl]propan-2-yl}-3-(3-methyl-1azabicyclo[2.2.2]oct-3-yl)urea;

2-(1-azabicyclo[3.2.2]non-4-yl)-N-[1-(5-phenylpyridin-2-yl)cyclopropyl]acetamide;

3-(4'-fluorobiphenyl-4-yl)-3-methyl-N-(4-methyl-1-azabicyclo[3.2.2]non-4-5 yl)butanamide;

N-[2-(biphenyl-4-yl)propan-2-yl]-N'-(3-methyl-1-azabicyclo[2.2.2]oct-3-yl)sulfuric diamide;

N-[2-(4'-fluorobiphenyl-4-yl)propan-2-yl]-N'-(3-methyl-1-azabicyclo[2.2.2]oct-3-yl)sulfuric diamide;

1-(3-butyl-1-azabicyclo[2.2.2]oct-3-yl)-3-{2-[1-(4-fluorophenyl)-IH-pyrazol-4-yl]propan-2-yl}urea;

1-azabicyclo[2.2.2]oct-3-yl [4-(4-fluorophenyl)-2-methylbut-3-yn-2-yl]carbamate; 1-(3-butyl-1-azabicyclo[2.2.2]oct-3-yl)-3-[4-(4-fluorophenyl)-2-methylbut-3-yn-2-yl]urea;

N-[1-(4'-fluorobiphenyl-4-yl)cyclopropyl]-1,4-diazabicyclo[3.2.2]nonane-4-carboxamide;

1-(2-(4'-fluoro-[I,1'-biphenyl]-4-yl)propan-2-yl)-3-(3-methyl-1-azabicyclo[3.2.2]nonan-3-yl)urea;

1-(2-(4'-fluoro-[I,1'-biphenyl]-4-yl)propan-2-yl)-3-(4-methyl-1-azabicyclo[4.2.2]decan-4-yl)urea;

1-(2-(4'-fluoro-[I,1'-biphenyl]-4-yl)propan-2-yl)-3-(3-methyl-1-azabicyclo[4.2.2]decan-3-yl)urea; and 1-(2-(4'-fluoro-[1,1'-biphenyl]-4-yl)propan-2-yl)-3-(5-methyl-1-azabicyclo[4.2.2]decan-5-yl)urea.

Additional examples of GCS inhibitors are listed below.

((S)-Quinuclidin-3-yl (2-(4'-(2-methoxyethoxy)-[1,1'-biphenyl]-4-yl)propan-2-yl)carbamate)

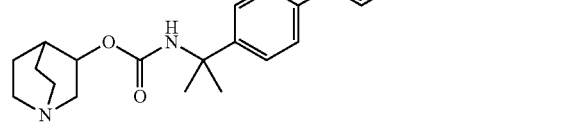

(4-Fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide)

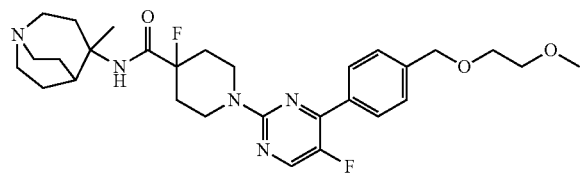 [SMILES: COCCOCc1ccc(-c2nc(N3CCC(F)(C(=O)NC4(C)CCN5CCC4CC5)CC3)ncc2F)cc1]

(4-Fluoro-1-(4-(4-((2-methoxyethoxy)methyl)phenyl)pyrimidin-2-yl)-N-(3-methylquinuclidin-3-yl)piperidine-4-carboxamide)

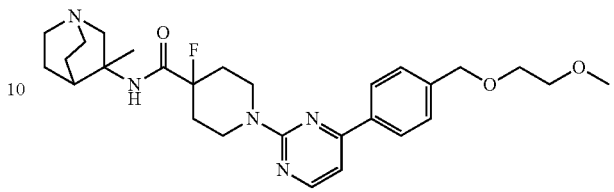

(4-Fluoro-1-(4-(4-((2-methoxyethoxy)methyl)phenyl)pyrimidin-2-yl)-N-(4-methyl-1-azabicyclo[3.2.2]nonan-4-yl)piperidine-4-carboxamide)

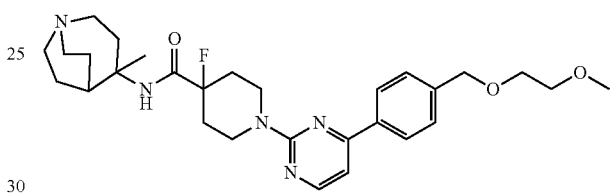

(4-Fluoro-1-(4-(4-(methoxymethyl)phenyl)pyrimidin-2-yl)-N-(3 methylquinuclidin-3-yl)piperidine-4-carboxamide)

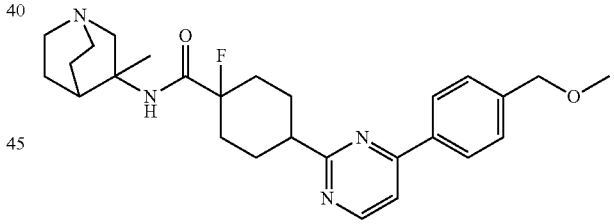

(4-Fluoro-1-(4-(4-(methoxymethyl)phenyl)pyrimidin-2-yl)-N-(4-methyl-1-azabicyclo[3.2.2]nonan-4-yl)piperidine-4-carboxamide)

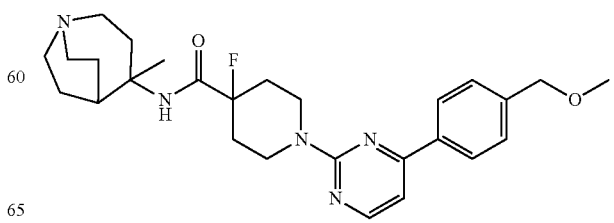

(4-Fluoro-1-(4-(4-(2-methoxyethoxy)phenyl)pyrimidin-2-yl)-N-(3-methylquinuclidin-3-yl)piperidine-4-carboxamide)

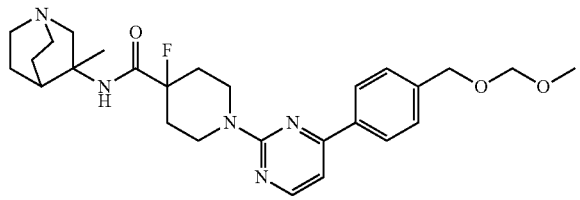 [SMILES: COCOCc1ccc(-c2ccnc(N3CCC(F)(C(=O)NC4(C)CN5CCC4CC5)CC3)n2)cc1]

(4-Fluoro-1-(4-(4-(2-methoxyethoxy)phenyl)pyrimidin-2-yl)-N-(4-methyl-1-azabicyclo[3.2.2]nonan-4-yl)piperidine-4-carboxamide)

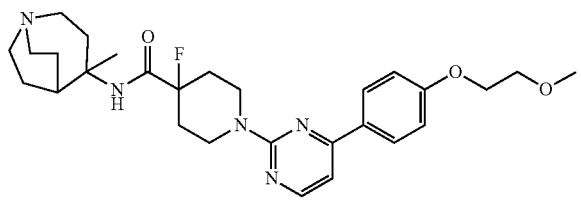 [SMILES: COCCOc1ccc(-c2ccnc(N3CCC(F)(C(=O)NC4(C)CCN5CCC4CC5)CC3)n2)cc1]

(4-Fluoro-1-(4-(4-(2-fluoroethoxy)phenyl)pyrimidin-2-yl)-N-(quinuclidin-3-yl)piperidine-4-carboxamide)

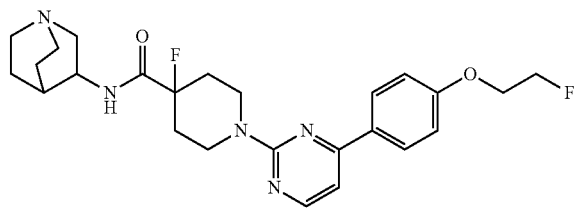 [SMILES: O=C(NC1CN2CCC1CC2)C1(F)CCN(c2nccc(-c3ccc(OCCF)cc3)n2)CC1]

(4-Fluoro-1-(4-(4-(2-fluoroethoxy)phenyl)pyrimidin-2-yl)-N-(4-methyl-1-azabicyclo[3.2.2]nonan-4-yl)piperidine-4-carboxamide)

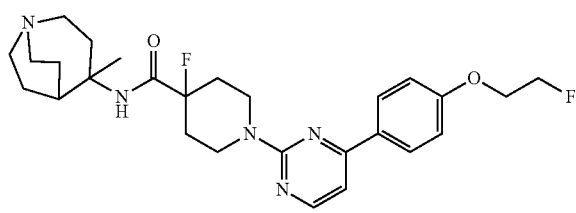 [SMILES: CC1(NC(=O)C2(F)CCN(c3nccc(-c4ccc(OCCF)cc4)n3)CC2)CCN2CCC1CC2]

Another exemplary GCS inhibitor is: carbamic acid, N-[1-[2-(4-fluorophenyl)-4-thiazolyl]-1-methylethyl]-,(3S)-1-azabicyclo[2.2.2]oct-3-yl ester as represented by Formula II below:

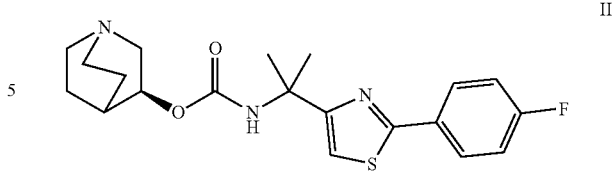

Another exemplary GCS inhibitor is: quinuclidin-3-yl (2-(4'-fluoro-[1,1'-biphenyl]-3-yl)propan-2-yl)carbamate as represented by Formula III below:

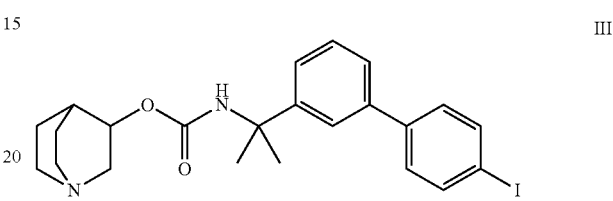

Some examples of a treatment for PKD include the administration of one or more cyclin dependent kinase (CDK) inhibitors. Non-limiting examples of CDK inhibitors include S-CR8, olomoucine, LEE011, palbociclib, P1446A-05, PD-0332991, and R-roscovitine. Additional examples of CDK inhibitors are described in Cicenas et al. (*J. Cancer Res. Clin. Oncol.* 138:1409-1418, 2011), Blachly et al. (*Leuk. Lymphoma* 54:2133-2143, 2013), Galons et al. (*Expert Opin. Ther. Pat.* 20:377-404, 2010), Geyer et al. (*Biochim. Biophys. Acta* 1754:160-170, 2005). Additional examples of CDK inhibitors are described in U.S. Patent Application Publication Nos. 2006/0178371, 2006/0173017, 2006/0173016, 2006/0135589, 2006/0128725, 2006/0106023, 2006/0041131, 2006/0040958, 2006/0030555, 2005/0261353, 2005/0130980, 2005/0004007, 2004/0248905, 2004/0209878, 2004/0198757, 2004/0116442, 2004/0110775, 2004/0106624, 2004/0102451, 2004/0097517, 2004/0097516, 2004/0073969, 2004/0072835, 2004/0063715, 2004/0048849, 2004/0006074, 2003/0073686, 2002/0065293, 2002/0042412, 2002/0013328, 2002/0002178, and 2001/0025379.

Another example of a treatment for PKD is hemodialysis or peritoneal dialysis. A further example of a treatment for PKD is the surgical transplantation of a kidney.

Determination of a Level of a Marker(s)

The methods provided herein include the determination of the level(s) of a marker(s) (e.g., AMBP and/or AMBP and at least one additional marker of PKD), in at least one sample from a patient (e.g., a PKD patient). For example, the level(s) of a marker(s) (e.g., AMBP and/or AMBP and at least one additional marker of PKD) can be determined in a sample including a biological fluid (e.g., urine) or kidney tissue (e.g., a kidney biopsy sample) from the patient (e.g., a PKD patient). In some examples, the marker(s) is a protein. In other examples, the marker(s) is an mRNA encoding the marker protein.

Methods for determining the levels of the marker(s) described herein (e.g., AMBP or AMBP and one or more additional markers of PKD) are well understood in the art. For example, the protein level(s) of a marker(s) described herein (e.g., AMBP or AMBP and one or more additional markers of PKD) can be determined using an antibody-based assay (e.g., an enzyme-linked immunosorbent assay, antibody array, antibody-labeled beads, or immunoblots).

Exemplary antibodies that can be used in these antibody-based assays are described in the Examples. Additional antibodies that can be used in the antibody-based assays are known in the art. Non-limiting examples of antibodies that specifically bind to human AMBP are commercially available from Santa Cruz Biotechnology (Dallas, TX), Thermo Fisher Scientific (Waltham, MA), and Altas Antibodies (Stockholm, Sweden). Non-limiting examples of antibodies that specifically bind to PCNA are commercially available from Santa Cruz Biotechnology (Dallas, TX), Abcam (Cambridge, MA), and Acris Antibodies (San Diego, CA). Non-limiting examples of antibodies that specifically bind to cyclin D1 are commercially available from Santa Cruz Biotechnology (Dallas, TX), Cell Signaling Technology (Danvers, MA), and Abcam (Cambridge, MA). Non-limiting examples of antibodies that specifically bind to cyclin D3 are commercially available from Santa Cruz Biotechnology (Dallas, TX), Abcam (Cambridge, MA), and Novus Biologicals (Littleton, CO). Non-limiting examples of antibodies that specifically bind to MEK are commercially available from Santa Cruz Biotechnology (Dallas, TX), Sigma-Aldrich (St. Louis, MO), and Cell Signaling Technology (Danvers, MA). Non-limiting examples of antibodies that specifically bind to S6 are commercially available from Santa Cruz Biotechnology (Dallas, TX), Thermo Fisher Scientific (Waltham, MA), and GenWay Biotech. Inc. (San Diego, CA). Non-limiting examples of antibodies that specifically bind to pS6 are commercially available from Cell Signaling Technology (Danvers, MA), Abcam (Cambridge, MA), and Abbiotec (San Diego, CA). Non-limiting examples of antibodies that specifically bind to ERK are commercially available from Cell Signaling Technology (Danvers, MA), Santa Cruz Biotechnology (Dallas, TX), and Thermo Fisher Scientific (Waltham, MA). Non-limiting examples of antibodies that specifically bind to pERK are commercially available from Cell Signaling Technologies (Danvers, MA), EMD Millipore (Billerica, MA), and eBioscience (San Diego, CA). Non-limiting examples of antibodies that specifically bind to AKT are commercially available from Cell Signaling Technologies (Danvers, MA), Abcam (Cambridge, MA), and Santa Cruz Biotechnology (Dallas, TX). Non-limiting examples of antibodies that specifically bind to pAkt are commercially available from Cell Signaling Technologies (Dallas, TX), EMD Millipore (Billerica, MA), and Signalway Antibody (College Park, MD). Non-limiting examples of antibodies that specifically bind to caspase-2 are commercially available from Santa Cruz Biotechnology (Dallas, TX), Acris Antibodies (San Diego, CA), and Abcam (Cambridge, MA). A non-limiting example of an antibody that specifically binds to RBBP is commercially available from Santa Cruz Biotechnology (Dallas, TX).

Methods of making antibodies that specifically bind to a marker (e.g., AMBP or any of the additional markers of PKD described herein) are also well known in the art. Additional methods for determining the protein level(s) of the marker(s) include mass spectrometry, liquid chromatography (e.g., high performance liquid chromatography) mass spectrometry (LC-MS), and liquid chromatography (e.g., high performance liquid chromatography) tandem mass spectrometry (LC-MS/MS). Non-limiting examples of methods for determining a protein level of a marker in a sample including a biological fluid are described in Pisitkun et al. (*Proteomics Clin. Appl.* 6:268-278, 2012). These exemplary methods of determining the level(s) of the marker(s) (e.g., AMBP or AMBP and at least one additional marker of PKD) can be used in any of the methods provided herein.

The mRNA level(s) of the marker(s) described herein (e.g., AMBP or AMBP and at least one additional marker of PKD) can be determined, e.g., using a polymerase chain reaction (PCR)-based assay (e.g., real-time PCR and reverse-transcriptase PCR). Additional methods for determining the mRNA level of each marker include the use of a gene chip. Further examples of methods for determining the mRNA level of a marker in a sample including a biological fluid are described in Chen et al. (*Lab Chip* 10:505-511, 2010), Schageman et al. (*BioMed Res. Int., Article ID* 253957, 2013), and Alvarez et al. (*Kidney Inter.* 82:1024-1032, 2012). Additional methods for determining an mRNA level of a marker are well known in the art.

In some examples, a sample (e.g., a sample comprising a biological fluid or kidney tissue, such as a kidney biopsy sample) from a subject can be stored for a period of time (e.g., stored at least 1 hour (e.g., at least 2, 4, 6, 8, 12, or 24 hours, or at least 1, 2, 3, 4, 5, 6, 7, 14, or 21 days, e.g., at a temperature of about 10° C., about 0° C., about −20° C., about −40° C., about −70° C., or about −80° C.) before the level(s) of the marker(s) are determined in the sample. Some examples further include a step of concentrating a sample including a biological fluid before the level(s) of the marker (s) (e.g., AMBP or AMBP and at least one additional marker of PKD) is determined.

The level(s) of AMBP (and optionally the level(s) at least one additional marker of PKD) can be determined in a sample (e.g., a sample including a biological fluid or kidney tissue (e.g., a kidney biopsy sample) in any of the methods described herein. A description of AMBP and exemplary additional markers of PKD is provided below.

AMBP

Alpha-1-microglobulin/bikunin precursor (AMBP) is a 39 kDa pre-pro-protein having 352 amino acids. The amino acid sequence of human AMBP is shown in SEQ ID NO: 1. AMBP is typically digested intracellularly to first remove a signal sequence (the first 19 amino acids of SEQ ID NO: 1) to yield a pro-protein (illustrated herein as SEQ ID NO: 2), and then is further cleaved by proteases to yield three different downstream protein products: alpha-1-microglobulin (having an amino acid sequence shown in SEQ ID NO: 3), bikunin (having an amino acid sequence shown in SEQ ID NO: 4), and trypstatin (having an amino acid sequence shown in SEQ ID NO: 5). Human AMBP (i.e., SEQ ID NO: 1) may be glycosylated at one or more of the following amino acid positions in SEQ ID NO: 1: the threonine at amino acid position 24, the asparagine at amino acid position 36, the asparagine at amino acid position 115, the serine at amino acid position 215, and the asparagine at amino acid position 250. When measuring a protein level of AMBP, the level measured can include the non-glycosylated form of AMBP and one or more forms of AMBP that has been glycosylated at one or more amino acid positions.

Additional Markers of PKD

In any of the methods described herein, a level or multiple level(s) of at least one (e.g., two, three, four, five, six, seven, eight, nine, ten, eleven, twelve, or thirteen) additional marker of PKD can be determined (e.g., in any combination such as those described in U.S. Provisional Patent Application Ser. No. 62/033,031). Non-limiting examples of additional markers of PKD are described below.

PCNA

Proliferating Cell Nuclear Antigen (PCNA) is a 28.8 kDa protein having 261 amino acids. The amino acid sequence of human PCNA is shown in SEQ ID NO: 6. When measuring a protein level of PCNA, the level measured can include the forms of PCNA that are non-phosphorylated and phosphorylated at the tyrosine at amino acid position 248 in SEQ ID NO: 6, include only the form of PCNA phosphorylated at the tyrosine at amino acid position 248 in SEQ ID NO: 6, or include only the unphosphorylated form of PCNA.

Cyclin D1

Cyclin D1 is a 33.7 kDa protein having 295 amino acids. The amino acid sequence of human cyclin D1 is shown in SEQ ID NO: 7. When measuring a protein level of cyclin D1, the level measured can include the forms of cyclin D1 that are non-phosphorylated and phosphorylated at the threonine at amino acid position 286 in SEQ ID NO: 7, include only the form of cyclin D1 phosphorylated at the threonine at amino acid position 286 in SEQ ID NO: 7, or include only the unphosphorylated form of cyclin D1.

Cyclin D3

Cyclin D3 is a protein having 292 amino acids. The amino acid sequence of human cyclin D3 is shown in SEQ ID NO: 8. When measuring a protein level of cyclin D3, the level measured can include the forms of cyclin D3 that are non-phosphorylated and phosphorylated at the serine at amino acid position 279 in SEQ ID NO: 8, include only the form of cyclin D3 phosphorylated at the serine at amino acid position 279 in SEQ ID NO: 8, or include only the unphosphorylated form of cyclin D3.

MEK

MAPK-ERK kinase 1 (MEK) is a protein having two isoforms. The first isoform of human MEK has a sequence of 393 amino acids (as shown in SEQ ID NO: 9) and the second isoform of human MEK has a sequence of 367 amino acids (as shown in SEQ ID NO: 10). When measuring the protein level of MEK, the level can include one or more of: the unphosphorylated form of the first isoform of MEK; the unphosphorylated form of the second isoform of MEK; one or more form(s) of the first isoform of MEK including one or more of a phosphorylation at the serine at amino acid position 218 in SEQ ID NO: 9, a phosphorylation at the serine at amino acid position 222 in SEQ ID NO: 9, a phosphorylation at the threonine at amino acid position 286 in SEQ ID NO: 9, a phosphorylation at the threonine at amino acid position 292 in SEQ ID NO: 9, and a phosphorylation at the serine at amino acid position 298 in SEQ ID NO: 9; and one or more form(s) of the second isoform of MEK including one or more of a phosphorylation at the serine at amino acid position 192 of SEQ ID NO: 10, a phosphorylation at the serine at amino acid position 196 of SEQ ID NO: 10, a phosphorylation at the threonine at amino acid position 260 in SEQ ID NO: 10, a phosphorylation at the threonine at amino acid position 266 in SEQ ID NO: 10, and a phosphorylation at the serine at amino acid position 272 in SEQ ID NO: 10.

S6, pS6, and Total S6

Ribosomal protein S6 (S6) is a 28.7 kDa protein having 249 amino acids. The amino acid sequence of human S6 is shown in SEQ ID NO: 11. The phrase "level of S6," "total S6," or "level of ribosomal protein S6," when referring to a protein level can include the sum of the levels of all detectable forms (e.g., all phosphorylated forms and the unphosphorylated form) of S6. The phosphorylated forms of S6 protein can include one or more of: a phosphorylation of the serine at amino acid position 235 in SEQ ID NO: 11, a phosphorylation of the serine at amino acid position 236 in SEQ ID NO: 11, a phosphorylation of the serine at amino acid position 240 in SEQ ID NO: 11, a phosphorylation at the serine at amino acid position 242 in SEQ ID NO: 11, a phosphorylation at serine at amino acid position 244 in SEQ ID NO: 11, and a phosphorylation at the serine at amino acid position 247 in SEQ ID NO: 11. In some embodiments, the level of S6 can be determined with an antibody that binds to an antigen common to all detectable forms (e.g., all phosphorylated forms and the unphosphorylated form) of S6.

The phrase "level of pS6" or "level of ribosomal protein pS6," when referring to a protein level, means the level (or sum of two or more of the levels) of one or more of a phosphorylated form of ribosomal S6 protein having a phosphorylation at serine at amino acid position 235 in SEQ ID NO: 11, a phosphorylation at serine at amino acid position 236 in SEQ ID NO: 11, or a phosphorylation in the serines at amino acid positions 235 and 236 in SEQ ID NO: 11. The level of pS6 can be determined, e.g., using an antibody or antibodies that specifically bind to an epitope in S6 that includes the phosphorylated serine at amino acid position 235 in SEQ ID NO: 11 and/or the phosphorylated serine at amino acid position 236 in SEQ ID NO: 11.

ERK

The phrase "level of ERK," when referring to a protein level, can include the sum of the levels of all detectable forms of ERK1 (e.g., all phosphorylated forms and unphosphorylated forms of each isoform of ERK1) and/or all detectable forms of ERK2 (e.g., all phosphorylated forms and unphosphorylated forms). The first isoform of human ERK1 has a sequence of 379 amino acids (as shown in SEQ ID NO: 12). The second isoform of human ERK1 has a sequence of 335 amino acids (as shown in SEQ ID NO: 13). The third isoform of human ERK1 has a sequence of 357 amino acids (as shown in SEQ ID NO: 14). The first isoform of human ERK2 has a sequence of 360 amino acids (as shown in SEQ ID NO: 15). The second isoform of human ERK2 has a sequence of 316 amino acids (as shown in SEQ ID NO: 16).

The phosphorylated forms of the first isoform of ERK1 can include one or more of: a phosphorylation of the serine at amino acid position 170 in SEQ ID NO: 12, a phosphorylation of the threonine at amino acid position 198 in SEQ ID NO: 12, a phosphorylation of the threonine at amino acid position 202 in SEQ ID NO: 12, a phosphorylation of the tyrosine at amino acid position 204 in SEQ ID NO: 12, and a phosphorylation of the threonine at amino acid position 207 in SEQ ID NO: 12. The phosphorylated forms of the second isoform of ERK1 can include one or more of: phosphorylation of the serine at amino acid position 170 in SEQ ID NO: 13, a phosphorylation of the threonine at amino acid position 198 in SEQ ID NO: 13, a phosphorylation of the threonine at amino acid position 202 in SEQ ID NO: 13, a phosphorylation of the tyrosine at amino acid position 204 in SEQ ID NO: 13, and a phosphorylation of the threonine at amino acid position 207 in SEQ ID NO: 13. The phosphorylated forms of the third isoform of ERK1 can include one or more of: a phosphorylation of the serine at amino acid position 170 in SEQ ID NO: 14, a phosphorylation of the threonine at amino acid position 198 in SEQ ID NO: 14, a phosphorylation of the threonine at amino acid position 202 in SEQ ID NO: 14, a phosphorylation of the tyrosine at amino acid position 204 in SEQ ID NO: 14, and a phosphorylation of the threonine at amino acid position 207 in SEQ ID NO: 14. All detectable forms of ERK1 can be identified, e.g., with an antibody that specifically binds to an epitope shared between the unphosphorylated forms of the first, second, and third isoforms of ERK1 and all of the various phosphorylated forms of the first, second, and third isoforms of ERK1.

The phosphorylated forms of the first isoform of ERK2 can include one or more of: a phosphorylation at the serine at amino acid position 29 in SEQ ID NO: 15, a phosphorylation of the threonine at amino acid position 185 in SEQ ID NO: 15, a phosphorylation of the tyrosine at amino acid position 187 in SEQ ID NO: 15, a phosphorylation of the threonine at the amino acid position 190 in SEQ ID NO: 15, a phosphorylation of the serine at the amino acid position 246 in SEQ ID NO: 15, a phosphorylation of the serine at amino acid position 248, and a phosphorylation of the serine at amino acid position 284 in SEQ ID NO: 15. The phosphorylated forms of the second isoform of ERK2 can include one or more of: a phosphorylation at the serine at amino acid position 29 in SEQ ID NO: 16, a phosphorylation of the threonine at amino acid position 185 in SEQ ID NO: 16, a phosphorylation of the tyrosine at amino acid position 187 in SEQ ID NO: 16, and a phosphorylation of the threonine at the amino acid position 190 in SEQ ID NO: 16. All detectable forms of ERK2 can be identified, e.g., using an antibody that specifically binds to an epitope shared between the unphosphorylated forms of the first and second isoforms of ERK2 and all of the various phosphorylated forms of the first and second isoforms of ERK2.

pERK

The phrase "level of pERK," when referring to a protein level can include the level (or sum of two or more of the levels) of one or more of: a form of the first isoform of ERK1 having a phosphorylation at the threonine at amino acid position 202 in SEQ ID NO: 12, a form of the first isoform of ERK1 having a phosphorylation at the tyrosine at amino acid position 204 in SEQ ID NO: 12, a first isoform of ERK1 having a phosphorylation at threonine at amino acid position 202 and tyrosine at amino acid position 204 in SEQ ID NO: 12, a form of the second isoform of ERK1 having a phosphorylation at the threonine at amino acid position 202 in SEQ ID NO: 13, a form of the second isoform of ERK1 having a phosphorylation at the tyrosine at amino acid position 204 in SEQ ID NO: 13, a form of the second isoform of ERK1 having a phosphorylation at the threonine at amino acid position 202 and the tyrosine at amino acid position 204 of SEQ ID NO: 13, a form of the third isoform of ERK1 having a phosphorylation at the threonine at amino acid position 202 in SEQ ID NO: 14, a form of the third isoform of ERK1 having a phosphorylation at the tyrosine at amino acid position 204 in SEQ ID NO: 14, a form of the third isoform of ERK1 having a phosphorylation at the threonine at amino acid position 202 and the tyrosine at amino acid position 204 in SEQ ID NO: 14, a form of the first isoform of ERK2 having a phosphorylation at the threonine at amino acid position 185 in SEQ ID NO: 15, a form of the first isoform of ERK2 having a phosphorylation at the tyrosine at amino acid position 187 of SEQ ID NO: 15, a form of the first isoform of ERK2 having a phosphorylation at the threonine at amino acid position 185 and the tyrosine at amino acid position 187 of SEQ ID NO: 15, a form of the second isoform of ERK2 having a phosphorylation at the threonine at amino acid position 185 in SEQ ID NO: 16, a form of the second isoform of ERK2 having a phosphorylation at the tyrosine at amino acid position 187 in SEQ ID NO: 16, and a form of the second isoform of ERK2 having a phosphorylation at the threonine at amino acid position 185 and the tyrosine at amino acid position 187 in SEQ ID NO: 16. The level of pERK can be determined, e.g., using an antibody that specifically binds to an epitope in the first, second, or third isoforms of ERK1 that includes the phosphorylated threonine at amino acid position 202 in SEQ ID NO: 12, 13, or 14 and/or the phosphorylated tyrosine at amino acid position 204 in SEQ ID NO: 12, 13, or 14, respectively, or an antibody that specifically binds to an epitope on the first or second isoforms of ERK2 that includes the phosphorylated threonine at amino acid position 185 in SEQ ID NO: 15 or 16 and/or the phosphorylated tyrosine at amino acid position 187 in SEQ ID NO: 15 or 16, respectively.

Akt

Akt is a 55.7 kDa protein having 480 amino acids (as shown in SEQ ID NO: 17). When measuring the protein level of Akt, the level can include two or more of: the unphosphorylated form of Akt and one or more form(s) of Akt including one or more of a phosphorylation at the serine at amino acid position 124 in SEQ ID NO: 17, a phosphorylation at the serine at amino acid position 126 in SEQ ID NO: 17, a phosphorylation at the serine at amino acid position 129 in SEQ ID NO: 12, a phosphorylation at the tyrosine at amino acid position 176 in SEQ ID NO: 17, a phosphorylation at the threonine at amino acid position 308 in SEQ ID NO: 17, a phosphorylation at the threonine at amino acid position 450 in SEQ ID NO: 17, a phosphorylation at the serine at amino acid position 473 in SEQ ID NO: 17, and a phosphorylation at the tyrosine at amino acid position 474 in SEQ ID NO: 17.

pAkt

The phrase "level of pAkt," when referring to a protein level can include the level (or sum of two or more of the levels) of one or more a form Akt having a phosphorylation at the serine at amino acid position 473 in SEQ ID NO: 17. The level of pAkt can be determined, e.g., by using an antibody that specifically binds to an epitope in Akt that includes the phosphorylated serine at amino acid position 473 in SEQ ID NO: 17.

Caspase-2

There are three different isoforms of caspase-2 in humans. The first isoform of caspase-2 in its unprocessed form has a total of 452 amino acids (as shown in SEQ ID NO: 18). After processing, the first isoform of caspase-2 forms three subunit peptides: amino acids 170-325 of SEQ ID NO: 18 (caspase-2 subunit p18), amino acids 334-452 of SEQ ID NO: 18 (caspase-2 subunit p13), and amino acids 348-452 of SEQ ID NO: 18 (caspase-2 subunit p12). Amino acids 2-169 of SEQ ID NO: 18 represent the prosequence of the unprocessed form of caspase-2. The second isoform has a total of 313 amino acids (SEQ ID NO: 19). The third isoform has a total of 91 amino acids (SEQ ID NO: 20). A phosphorylated form of the first isoform of caspase-2 has a phosphorylation at the serine at amino acid position 340 in SEQ ID NO: 18. When measuring the protein level of caspase-2, the level can include one or more of the unprocessed form of the first isoform of caspase-2, the caspase-2 subunit p18, the caspase-2 subunit p13, the caspase-2 subunit p12, the form of the first isoform of caspase-2 having a phosphorylation at the serine at amino acid position 340 in SEQ ID NO: 18, and a form of the caspase-2 subunit p13 having a phosphorylation at the serine at amino acid position 7 in caspase-2 subunit p13.

RBBP

Human retinoblastoma binding protein (RBBP) has 425 amino acids (as shown in SEQ ID NO: 21). A phosphorylated form of RBBP has a phosphorylation at the serine at amino acid position 110 in SEQ ID NO: 21. When measuring the protein level of RBBP, the level can include one or both of: the unphosphorylated form of RBBP and a form of RBBP having a phosphorylation at the serine at amino acid position 110 in SEQ ID NO: 21.

Methods of Determining the Efficacy of a Treatment of PKD

Provided herein are methods of determining the efficacy of a treatment for PKD (e.g., ADPKD or ARPKD) in a PKD patient. In some examples, these methods include: (a) providing a first sample including a biological fluid (e.g., urine)

or kidney tissue (e.g., a kidney biopsy sample) obtained from a PKD patient; (b) determining a level of AMBP in the first sample; (c) administering a treatment for PKD to the PKD patient; (d) providing a second sample including a biological fluid (e.g., urine) or kidney tissue (e.g., a kidney biopsy sample) from the PKD patient after step (c) and determining a level of AMBP in the second sample; and (e) identifying the administered treatment as being effective if the level in the second sample is lower than the level in the first sample. In some examples, these methods include (a) providing a first sample including a biological fluid (e.g., urine) or kidney tissue (e.g., a kidney biopsy sample) obtained from a PKD patient; (b) determining a level of AMBP and a level(s) of at least one (e.g., two, three, four, five, six, seven, eight, nine, ten, eleven, twelve, or thirteen) additional marker of PKD (e.g., PCNA, cyclin D1, cyclin D3, MEK, S6, pS6, ERK, pERK, Akt, pAkt, caspase-2, total S6, and RBBP) in the first sample; (c) administering a treatment for PKD to the PKD patient; (d) providing a second sample including a biological fluid (e.g., urine) or kidney tissue (e.g., a kidney biopsy sample) from the PKD patient after step (c) and determining a level of AMBP and the level(s) of the at least one additional marker of PKD in the second sample; and (e) identifying the administered treatment as being effective if (i) the AMBP level in the second sample is lower than the AMBP level in the first sample, and (ii) the level of one (or the levels of two, three, four, five, six, seven, eight, nine, ten, eleven, twelve, or thirteen) of the at least one additional marker of PKD in the second sample is lower than the level(s) of the at least one additional marker of PKD in the first sample.

Some embodiments further include after (e): (f) administering additional doses of the administered GCS inhibitor identified as being effective (e.g., (S)-quinuclidin-3-yl (2-(4'-(2-methoxyethoxy)-[1,1'-biphenyl]-4-yl)propan-2-yl) carbamate; 4-fluoro-1-(5-fluoro-4-(4-((2-methoxyethoxy) methyl)phenyl)pyrimidin-2-yl)-N-(4-methyl-1 azabicyclo [3.2.2]nonan-4-yl)piperidine-4-carboxamide; 4-fluoro-1-(4-(4-((2-methoxyethoxy)methyl) phenyl) pyrimidin-2-yl)-N-(3-methylquinuclidin-3-yl)piperidine-4-carboxamide; 4-fluoro-1-(4-(4-((2-methoxyethoxy)methyl)phenyl)pyrimidin-2-yl)-N-(4-methyl-1-azabicyclo[3.2.2]nonan-4-yl)piperidine-4-carboxamide; 4-fluoro-1-(4-(4-(methoxymethyl) phenyl)pyrimidin-2-yl)-N-(3-methylquinuclidin-3-yl)piperidine-4-carboxamide; 4-fluoro-1-(4-(4-(methoxymethyl) phenyl)pyrimidin-2-yl)-N-(4-methyl-1-azabicyclo[3.2.2] nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy) phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl)pyrimidin-2-yl)-N-(quinuclidin-3-yl)piperidine-4-carboxamide; 4-fluoro-1-(4-(4-(2-fluoroethoxy)phenyl)pyrimidin-2-yl)-N-(4-methyl-1-azabicyclo[3.2.2]nonan-4-yl)piperidine-4-carboxamide); carbamic acid, N-[1-[2-(4-fluorophenyl)-4-thiazolyl]-1-methylethyl]-, (3S)-1-azabicyclo[2.2.2]oct-3-yl ester (as represented by Formula II); or quinuclidin-3-yl (2-(4'-fluoro-[1,1'-biphenyl]-3-yl)propan-2-yl)carbamate (as represented by Formula III)) to the PKD patient. Some examples of the methods further include after (e): (0 administering additional doses of the administered treatment identified as being effective (e.g., a CDK inhibitor, such as S-CR8) to the PKD patient.

In some embodiments, the steps (b) and (d) include determining the level of one (or the levels of two, three, four, five, or six) additional marker(s) of PKD selected from the group of: PCNA, cyclin D1, cyclin D3, MEK, S6, and pS6, and the administered treatment is identified as being effective if (i) the AMBP level in the second sample is lower than the AMBP level in the first sample, and (ii) the level of one (or the levels of two, three, four, five, or six) of the additional marker(s) of PKD in the second sample is less than the level(s) of the at least one additional marker of PKD in the first sample.

In some examples, the determining the levels of AMBP and optionally, the determining of the level of at least one additional biomarker of PKD in (b) and (d) includes determining the protein levels of AMBP and optionally, the protein level(s) of at least one additional marker of PKD. For example, the determining in (b) and (d) can include contacting the samples with antibodies that bind specifically to AMBP protein, and optionally antibodies that bind specifically to the at least one additional marker of PKD. In some embodiments, (b) and (d) include determining the protein level of the additional marker(s) of PKD of one or both of cyclin D1 and MEK.

In some embodiments of any of the methods, the administered treatment in (c) is administration of a glucosyl ceramide synthase (GCS) inhibitor (e.g., any of the GCS inhibitors described herein or known in the art). For example, the GCS inhibitor is selected from the group of: (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2methoxyethoxy)methyl) phenyl)pyrimidin-2-yl)-N-(4-methyl-1-azabicyclo[3.2.2]nonan-4-yl)piperidine-4-carboxamide; 4-fluoro-1-(4-(4-((2-methoxyethoxy)methyl) phenyl)pyrimidin-2-yl)-N-(3-methylquinuclidin-3-yl) piperidine-4-carboxamide; 4-fluoro-1-(4-(4-((2-methoxyethoxy) methyl)phenyl)pyrimidin-2-yl)-N-(4-methyl-1-azabicyclo[3.2.2]nonan-4-yl)piperidine-4-carboxamide; 4-fluoro-1-(4-(4-(methoxy methyl)phenyl) pyrimidin-2-yl)-N-(3-methylquinuclidin-3-yl)piperidine-4-carboxamide; 4-fluoro-1-(4-(4-(methoxy methyl) phenyl) pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy) phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; 4-fluoro-1-(4-(4-(2-fluoroethoxy) phenyl) pyrimidin-2-yl)-N-(4-methyl-1-azabicyclo[3.2.2]nonan-4-yl)piperidine-4-carboxamide; carbamic acid, N-[1-[2-(4-fluorophenyl)-4-thiazolyl]-1-methylethyl]-, (3S)-1-azabicyclo[2.2.2]oct-3-yl ester (as represented by Formula II); and quinuclidin-3-yl (2-(4'-fluoro-[1,1'-biphenyl]-3-yl) propan-2-yl)carbamate (as represented by Formula III).

In some embodiments of any of the methods, the administered treatment in (c) is administration of a CDK inhibitor (e.g., any of the CDK inhibitors described herein or known in the art, such as R-roscovitine) to the PKD patient.

Some embodiments of any of the methods further include a step of selecting a patient having PKD or diagnosing a patient having PKD (e.g., using any of the exemplary methods of diagnosing PKD described herein). The patient in any of these methods can be any of the patients described herein. For example, a patient having PKD can have previously been administered a treatment for PKD and the treatment was unsuccessful. Some embodiments of any of the methods further include obtaining the first and/or second samples from the PKD patient.

Some embodiments further include recording the identified efficacy of the administered treatment in the patient's medical record (e.g., a computer readable medium). Some examples further include informing the patient, the patient's family, and/or the patient's primary care physician or attending physician of the identified efficacy of the administered treatment. Some embodiments further include authorizing a refill of an administered treatment identified as being effective.

The difference in time between when the first sample is obtained from the PKD patient and when the second sample is obtained from the PKD subject can be, e.g., between 1 week and 40 weeks, between 1 week and 30 weeks, between 1 week and 20 weeks, between 1 week and 12 weeks, between 1 week and 8 weeks, between 1 week and 4 weeks, between 1 week and 2 weeks, between 2 weeks and 12 weeks, between 2 weeks and 8 weeks, or between 2 weeks and 4 weeks.

Methods of Diagnosing PKD

Also provided are methods of diagnosing PKD (e.g., ADPKD or ARPKD) in a patient that include (a) providing a sample including a biological fluid (e.g., urine) or kidney tissue (e.g., kidney biopsy sample) from a patient suspected of having PKD; (b) determining a level of AMBP in the sample; and (c) identifying the patient as having PKD if the AMBP level is elevated, e.g., where the AMBP level exceeds a control level (e.g., a pre-determined threshold level).

In some examples, the methods of diagnosing PKD (e.g., ADPKD or ARPKD) in a patient include (a) providing a sample including a biological fluid (e.g., urine) or kidney tissue (e.g., kidney biopsy tissue) from a patient suspected of having PKD; (b) determining a level of AMP and determining a level(s) of at least one (e.g., two, three, four, five, six, seven, eight, nine, ten, eleven, twelve, or thirteen) additional marker of PKD (e.g., PCNA, cyclin D1, cyclin D3, MEK, S6, pS6, ERK, pERK, Akt, pAkt, caspase-2, total S6, and RBBP) in the sample; and (c) identifying the patient as having PKD if (i) the level of AMDA is elevated, e.g., as compared to a control level, and (ii) the level of one (or the levels of two, three, four, five, six, seven, eight, nine, ten, eleven, twelve, or thirteen) of the at least one additional markers of PKD is elevated as compared to a control level(s).

Some examples of these methods further include after (c): (d) administering a treatment for PKD (e.g., any of the exemplary treatments for PKD described herein) to a patient identified as having PKD. Some embodiments further include after (c): (d) administering a GCS inhibitor (e.g., (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2methoxyethoxy)methyl) phenyl)pyrimidin-2-yl)-N-(4-methyl-1-azabicyclo[3.2.2]nonan-4-yl)piperidine-4-carboxamide; 4-fluoro-1-(4-(4-((2-methoxyethoxy)methyl) phenyl)pyrimidin-2-yl)-N-(3-methylquinuclidin-3-yl) piperidine-4-carboxamide; 4-fluoro-1-(4-(4-((2-methoxyethoxy) methyl)phenyl)pyrimidin-2-yl)-N-(4-methyl-1-azabicyclo[3.2.2]nonan-4-yl)piperidine-4-carboxamide; 4-fluoro-1-(4-(4-(methoxymethyl)phenyl)pyrimidin-2-yl)-N-(3-methylquinuclidin-3-yl)piperidine-4-carboxamide; 4-fluoro-1-(4-(4-(methoxy methyl) phenyl) pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy) phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; 4-fluoro-1-(4-(4-(2-fluoroethoxy)phenyl) pyrimidin-2-yl)-N-(4-methyl-1-azabicyclo[3.2.2]nonan-4-yl)piperidine-4-carboxamide); carbamic acid, N-[1-[2-(4-fluorophenyl)-4-thiazolyl]-1-methylethyl]-, (3S)-1-azabicyclo[2.2.2]oct-3-yl ester (as represented by Formula II); or quinuclidin-3-yl (2-(4'-fluoro-[1,1'-biphenyl]-3-yl) propan-2-yl)carbamate (as represented by Formula III)) to a patient identified as having PKD. Some embodiments further include after (c): (d) administering a CDK inhibitor (e.g., roscovitine) to a patient identified as having PKD. Some embodiments further include after (c): (d) performing one or more additional tests to confirm PKD in the patient (e.g., performing imaging one or both kidney(s) in a patient identified as having PKD).

In some embodiments, the step (b) includes determining the level of one (or levels of two, three, four, five, six, or seven) of additional markers of PKD selected from the group of: PCNA, cyclin D1, cyclin D3, MEK, S6, and pS6, and the patient is identified as having PKD if the subject has a level of AMBP that is elevated as compared to a control level, and the level of one (or the levels of two, three, four, five, or six) of the additional marker(s) of PKD is elevated as compared to a control level.

In some examples, the determining the levels of AMBP and optionally, the determining of the level of at least one additional biomarker of PKD in (b) includes determining the protein level of AMBP and optionally, the protein level of at least one additional marker of PKD. For example, the determining in (b) can include contacting the sample with antibodies that bind specifically to AMBP protein, and optionally antibodies that bind specifically to the at least one additional marker of PKD. In some embodiments, (b) includes determining the protein level of the additional marker(s) of PKD of at least one of PCNA, cyclin D1, cyclin D3, MEK, S6, and pS6

In any of these methods, a control level can be a level, e.g., a level of AMBP (and optionally, also a level(s) of the at least one additional marker of PKD), in a subject not presenting with one or more symptoms of PKD and/or not diagnosed as having PKD, a level of the at least one marker in a healthy subject or a population of healthy subjects, or a threshold level (e.g., a level above which indicates that the subject has or may have PKD).

Some embodiments further include recording the identification of PKD in the patient in the patient's medical record (e.g., a computer readable medium). Some examples further include informing the patient, the patient's family, and/or the patient's primary care physician or attending physician of the identification of PKD in the patient. Some examples further include informing the patient's insurance provider of the identification of PKD in the patient.

Methods of Determining the Stage of PKD in a Patient

Also provided herein are methods of determining the stage of PKD (e.g., ADPKD or ARPKD) in a patient. Skilled practitioners will readily appreciate that determining the stage of PKD in a patient can be useful, e.g., in designing and administering a proper treatment regimen to treat the patient and thereby obtaining a desirable outcome. Exemplary methods can include: (a) providing a sample including a biological fluid (e.g., urine) or kidney tissue (e.g., kidney biopsy sample) from a patient suspected of having PKD or identified as having PKD; (b) determining a level of AMBP in the sample; and (c) determining the stage of PKD in the patient from the level. In some examples, the methods of determining the stage of PKD in a patient include: (a) providing a sample including a biological fluid (e.g., urine)

or kidney tissue (e.g., kidney biopsy sample) from a patient suspected of having PKD or identified as having PKD; (b) determining a level of AMBP and a level of at least one (e.g., two, three, four, five, six, seven, eight, nine, ten, eleven, twelve, or thirteen) additional marker of PKD (e.g., PCNA, cyclin D1, cyclin D3, MEK, S6, pS6, ERK, pERK, Akt, pAkt, caspase-2, total S6, and RBBP) in the sample; and (c) determining the stage of PKD in the patient from the level of AMBP and the level of one (or the levels of two, three, four, five, six, seven, eight, nine, ten, eleven, twelve, or thirteen) of the at least one additional markers of PKD.

In some embodiments, the determining in (b) includes comparing the determined level of AMBP (and optionally the level(s) of the at least one additional marker of PKD) to a range of values for a particular stage of PKD (e.g., stage I, stage II, stage III, stage IV, or stage V) and identifying a subject as having a particular stage of PKD if the level of AMBP (and optionally also the level of one (or the levels of two, three, four, five, six, seven, eight, nine, ten, eleven, twelve, or thirteen) of the at least one additional marker of PKD) falls within a range of values for the particular stage of PKD. Some embodiments further include after (c): (d) administering a treatment for stage I, stage II, stage III, stage IV, or stage V PKD to a patient identified as having stage I, stage II, stage III, stage IV, or stage V PKD, respectively. Some embodiments further include after (c): (d) performing one or more assays to confirm the stage of PKD (e.g., imaging one or both kidney(s) in a patient after (c) to confirm the stage of PKD in the patient). Some embodiments further include after (c): (d) hospitalizing a subject identified as having stage IV or stage V PKD. Ranges of levels of AMBP (and optionally also ranges of the level(s) of the at least one additional marker of PKD) in a sample including a biological fluid (e.g., urine) or kidney tissue (e.g., a kidney biopsy sample) from a subject having a certain stage of PKD (e.g., stage I, stage II, stage III, stage IV, or stage V PKD) can be determined using methods known in the art. The five stages of PKD are known in the art and descriptions of the stages are available in various publications. For example, the five stages are described on the Kidney Support webpage (kidney-support.org): stage 1 (emergence stage), stage 2 (growth stage), stage 3 (enlargement or swelling stage), stage 4 (cyst rupture stage), and stage 5 (end stage).

In some embodiments, step (b) includes determining a level (or levels of two, three, four, five, six, or seven) of additional markers of PKD selected from the group of: PCNA, cyclin D1, cyclin D3, MEK, S6, and pS6, and the stage of PKD is determined from the level of AMBP and a level (or levels of two, three, four, five, six, or seven) of the additional markers of PKD.

In some examples, the determining the levels of AMBP and optionally, the determining of the level of at least one additional biomarker of PKD in (b) includes determining the protein level of AMBP and optionally, the protein level of at least one additional marker of PKD. For example, the determining in (b) can include contacting the sample with antibodies that bind specifically to AMBP protein, and optionally antibodies that bind specifically to the at least one additional marker of PKD. In some embodiments, (b) includes determining the protein level of the additional marker(s) of PKD of at least one of PCNA, cyclin D3, MEK, and phosphorylated S6.

Methods of Monitoring PKD

Also provided are methods of monitoring a PKD patient (e.g., a ADPKD patient or a ARPKD patient). Monitoring can be useful, e.g., for observing a PKD patient's reaction to a given treatment and providing the skilled practitioner with information as to whether the treatment should be continued, modified, or stopped. Exemplary methods can include: (a) providing a first sample including a biological fluid (e.g., urine) or kidney tissue (e.g., a kidney biopsy sample) obtained from the PKD patient; (b) determining a level of AMBP in the first sample; (c) providing a second sample including a biological fluid (e.g., urine) or kidney tissue (e.g., a kidney biopsy sample) from the PKD patient after step (b) or after the first sample was obtained from the patient, and determining a level of AMBP in the second sample; and (d) identifying the patient as having improving or static PKD if the level in the second sample is not higher than the level in the first sample (or optionally, identifying the subject as having worsening or progressing PKD if the level in the second sample is higher than the level in the first sample).

Also provided are methods of monitoring a PKD patient that include: (a) providing a first sample including a biological fluid (e.g., urine) or kidney tissue (e.g., a kidney biopsy sample) obtained from the PKD patient; (b) determining a level of AMBP and a level(s) of at least one (e.g., two, three, four, five, six, seven, eight, nine, ten, eleven, twelve, or thirteen) additional marker of PKD (e.g., PCNA, cyclin D1, cyclin D3, MEK, S6, pS6, ERK, pERK, Akt, pAkt, caspase-2, total S6, and RBBP) in the first sample; (c) providing a second sample including a biological fluid (e.g., urine) or kidney tissue (e.g., a kidney biopsy sample) from the PKD patient after step (b) or after the first sample was obtained from the patient, and determining a level of AMBP and a level(s) of the at least one additional marker of PKD in the second sample; and (d) identifying the patient as having improving or static PKD if (i) the AMBP level in the second sample is not higher than the AMBP level in the first sample, and (ii) the level of one (or the levels of two, three, four, five, six, seven, eight, nine, ten, eleven, twelve, or thirteen) of the at least one additional marker of PKD in the second sample is not higher than the level(s) of the at least one additional marker of PKD in the first sample (or optionally, identifying the subject as having worsening or progressing PKD if (i) the AMBP level in the second sample is higher than the AMBP level in the first sample, and (ii) the level of one (or the levels of two, three, four, five, six, seven, eight, nine, ten, eleven, twelve, or thirteen) of the at least one additional marker of PKD in the second sample is higher than the level of the at least one additional marker(s) of PKD in the first sample).

In some embodiments, the steps (b) and (c) include determining the level of one (or the levels of two, three, four, five, or six) additional marker(s) of PKD selected from the group of: PCNA, cyclin D1, cyclin D3, MEK, S6, and pS6, and the patient is identified as having improving or static PKD if (i) the AMBP level in the second sample is not higher than the AMBP level in the first sample, and (ii) the level of one (or the levels of two, three, four, five, or six) of the additional marker(s) of PKD in the second sample is not higher than the level(s) of the at least one additional marker of PKD in the first sample (or optionally, the patient is identified as having worsening or progressing PKD if (i) the AMBP level in the second sample is higher than the AMBP level in the first sample, and (ii) the level of one (or the levels of two, three, four, five, or six) of the additional marker(s) of PKD in the second sample is higher than the level(s) of the at least one additional marker of PKD in the first sample).

In some embodiments, the steps (b) and (c) include determining the level of one (or the levels of two, three, four, five, or six) additional marker(s) of PKD selected from the group of: PCNA, cyclin D1, cyclin D3, MEK, S6, and pS6, and the patient is identified as having improving or static PKD if (i) the AMBP level in the second sample is not higher than the AMBP level in the first sample, and (ii) the level of one (or the levels of two, three, four, five, or six) of the additional marker(s) of PKD in the second sample is not higher than the level(s) of the at least one additional marker of PKD in the first sample (or optionally, the patient is identified as having worsening or progressing PKD if (i) the AMBP level in the second sample is higher than the AMBP level in the first sample, and (ii) the level of one (or the levels of two, three, four, five, or six) of the additional marker(s) of PKD in the second sample is higher than the level(s) of the at least one additional marker of PKD in the first sample).

In some examples, the determining the levels of AMBP and optionally, the determining of the level of at least one additional biomarker of PKD in (b) and (c) includes determining the protein levels of AMBP and optionally, the protein level(s) of at least one additional marker of PKD. For example, the determining in (b) and (c) can include contacting the samples with antibodies that bind specifically to AMBP protein, and optionally antibodies that bind specifically to the at least one additional marker of PKD. In some embodiments, (b) and (c) include determining the protein level of the additional marker(s) of PKD of at least one (e.g., two, three, or four) of PCNA, cyclin D3, MEK, and phosphorylated S6).

Some embodiments further include after (d): (e) administering the same treatment (e.g., any of the exemplary treatments of PKD described herein or known in the art) to a patient identified as having improving or static PKD. For example, the administering in (e) can be the administration of a GCS inhibitor (e.g., (S)-quinuclidin-3-yl (2-(4'-(2-methoxyethoxy)-[1,1'-biphenyl]-4-yl)propan-2-yl)carbamate; 4-fluoro-1-(5-fluoro-4-(4-((2methoxyethoxy)methyl) phenyl)pyrimidin-2-yl)-N-(4-methyl-1-azabicyclo[3.2.2] nonan-4-yl)piperidine-4-carboxamide; 4-fluoro-1-(4-(4-((2-methoxyethoxy)methyl)phenyl)pyrimidin-2-yl)-N-(3-methylquinuclidin-3-yl)piperidine-4-carboxamide; 4-fluoro-1-(4-(4-((2-methoxyethoxy) methyl)phenyl)pyrimidin-2-yl)-N-(4-methyl-1-azabicyclo[3.2.2]nonan-4-yl)piperidine-4-carboxamide; 4-fluoro-1-(4-(4-(methoxy methyl)phenyl) pyrimidin-2-yl)-N-(3-methylquinuclidin-3-yl)piperidine-4-carboxamide; 4-fluoro-1-(4-(4-(methoxy methyl) phenyl) pyrimidin-2-yl)-N-(4-methyl-1-azabicyclo[3.2.2]nonan-4-yl)piperidine-4-carboxamide; 4-fluoro-1-(4-(4-(2-methoxyethoxy)phenyl)pyrimidin-2-yl)-N-(3-methylquinuclidin-3-yl)piperidine-4-carboxamide; 4-fluoro-1-(4-(4-(2-methoxyethoxy) phenyl)pyrimidin-2-yl)-N-(4-methyl-1-azabicyclo[3.2.2]nonan-4-yl)piperidine-4-carboxamide; 4-fluoro-1-(4-(4-(2-fluoroethoxy)phenyl) pyrimidin-2-yl)-N-(quinuclidin-3-yl)piperidine-4-carboxamide; 4-fluoro-1-(4-(4-(2-fluoroethoxy)phenyl) pyrimidin-2-yl)-N-(4-methyl-1-azabicyclo[3.2.2]nonan-4-yl)piperidine-4-carboxamide); carbamic acid, N-[1-[2-(4-fluorophenyl)-4-thiazolyl]-1-methylethyl]-, (3S)-1-azabicyclo[2.2.2]oct-3-yl ester (as represented by Formula II); or quinuclidin-3-yl (2-(4'-fluoro-[1,1'-biphenyl]-3-yl) propan-2-yl)carbamate (as represented by compound of Formula III).

Some embodiments of any of the methods further include a step of selecting a patient having PKD or diagnosing a patient having PKD (prior to step (a)) (e.g., using any of the exemplary methods of diagnosing PKD described herein). The patient in any of these methods can be any of the patients described herein. Some embodiments of any of the methods further include obtaining the first and/or second samples from the PKD patient.

Some embodiments further include recording the improving or static PKD status (or alternatively the worsening or progressing status) of the patient in the patient's medical record (e.g., a computer readable medium). Some examples further include informing the patient, the patient's family, and/or the patient's primary care physician or attending physician of improving or static PKD status (or alternatively the worsening or progressing status) of the patient. Some embodiments further include authorization of a refill of a treatment administered to the patient between the time points when the first and second samples were obtained from the patient, when the patient has been identified as having improving or static PKD (or alternatively further include authorization not to refill a treatment administered to the patient between the time points when the first and second samples were obtained from the patient, when the patient has been identified as having worsening or progressing PKD). Some embodiments include discharging a subject from an inpatient facility (e.g., hospital) or decreasing inpatient treatments (e.g., dialysis) based on identification of the subject as having improving or static PKD (or include continuing impatient treatment (e.g., hospitalization) or increasing inpatient treatments (e.g., dialysis) of the subject based on identification of the subject as having worsening or progressing PKD).

The difference in time between when the first and second samples are obtained from the patient can be, e.g., between 1 week and 40 weeks, between 1 week and 30 weeks, between 1 week and 20 weeks, between 1 week and 12 weeks, between 1 week and 8 weeks, between 1 week and 4 weeks, between 1 week and 2 weeks, between 2 weeks and 12 weeks, between 2 weeks and 8 weeks, or between 2 weeks and 4 weeks.

Kits

Also provided herein are kits that consist essentially of or consist of an antibody that specifically binds to AMBP protein, and at least one (e.g., two, four, five, six, seven, eight, nine, ten, eleven, or twelve) antibody that specifically binds to an additional protein marker of PKD. For example, the kits can consist essentially of or consist of an antibody that specifically binds to AMBP protein and at least one (e.g., two, three, four, five, six, seven, eight, nine, ten, eleven, or twelve) antibody selected from the group consisting of: an antibody that specifically binds to PCNA, an antibody that specifically binds to cyclin D1, an antibody that specifically binds to cyclin D3, an antibody that specifically binds to MEK, an antibody that specifically binds to S6, an antibody that specifically binds to pS6, an antibody that specifically binds to ERK, an antibody that specifically binds to pERK, an antibody that specifically binds to Akt, an antibody that specifically binds to pAkt, an antibody that specifically binds to caspase-2, and an antibody that specifically binds to retinoblastoma binding protein (RBBP). In some examples, any combination of the antibody that specifically binds to AMBP protein and/or the at least one antibody that specifically binds to an additional protein marker of PKD are labeled (e.g., with a radioisotope, a fluorophore, or a quencher).

Some exemplary kits further include one or more positive control recombinant proteins (e.g., an isolated recombinant AMBP, PCNA, cyclin D1, cyclin D3, MEK, S6, pS6, ERK, pERK, Akt, pAkt, caspase-2, and RBBP). In some examples, the antibody that specifically binds to AMBP and the antibody that specifically binds to the at least one additional protein marker of PKD are covalently attached to a solid surface (e.g., a chip, a bead, or a membrane) by the Fc domain.

Some kits further include a sample including a biological fluid (e.g., a sample including a biological fluid, kidney tissue, or kidney cells) from a PKD patient (e.g., a PKD patient with a known severity of PKD) or an animal model of PKD (e.g., any of the animal models described in the Examples). Such samples are useful, e.g., as positive controls.

The invention is further described in the following examples, which do not limit the scope of the invention described in the claims.

EXAMPLES

Example 1. Identification of AMBP as a Marker of PKD and Levels of AMBP in Human PKD Patients and Two Different Mouse Models of PKD A set of experiments was performed to determine whether AMBP is an accurate marker of PKD in humans and in two different animal models of PKD.

Materials and Methods

Animals and Urine Collection $C_{57}BL/6J$ jck/+ mice were maintained for mating. Cystic jck/jck mice were genotyped as previously described (Smith et al., *J. Am. Soc. Nephrol.* 17:2821-2831, 2006). Pdk1 conditional knockout mice were generated as described previously (Natoli et al., *Nature Med.* 16:788-792, 2010). The Pdk1 gene was deleted by inducing the Cre recombinase activity with tamoxifen delivered in sunflower oil (Sigma-Aldrich, St. Louis, MO), on postnatal day 1 with 100 mg/kg.

Patient Sample Collection

Normal human patients and samples from human ADPKD patients were purchased from the National Disease Research Institute (NDRI). Urine samples from human ADPKD patients were collected at the University of Toronto. Briefly, mid void morning urine samples were collected and stabilized with Complete Proteinase Inhibitor Cocktail (Roche). The urine was centrifuged at 2000×g for 10 minutes to remove cellular debris and stored at −80° C. Total kidney volume (TKV) was quantified in ADPKD patients by magnetic resonance imaging (MRI) (without gadolinium) (Table 1).

TABLE 1

Profile of Patients Representing Early and Late Stage ADPKD with TKV 300-2000 mLs measured by MRI.

| Patient ID | age at MRI (yr) | Gender | Total Kidney Volume (ml) |
|---|---|---|---|
| 1 | 34 | f | 256 |
| 2 | 51 | f | 467 |
| 3 | 42 | f | 550 |
| 4 | 52 | f | 842 |
| 5 | 44 | f | 1091 |
| 6 | 46 | f | 1581 |
| 7 | 61 | f | 1689 |
| 8 | 41 | m | 1972 |

LC-MS/MS Sample Preparation

Proteoseek HAS/IgG antibody based removal kit (Pierce, Rockford, IL) was used to deplete albumin and the major subclasses of IgG from 100 µg of the urine samples. The depleted samples were precipitated in 10% (v/v) TCA (EMD Chemical) for 2 hours on ice. The precipitate was pelleted at 14000×g for 15 minutes and the supernatant was discarded. The pellet was washed with 200 µL acetone (−80° C.), vortexed, and re-pelleted at 14000×g for 10 minutes, and the supernatant discarded. The pellet was resuspended, reduced, alkylated, and trypsin digested using ProteaseMax degradable surfactant, and the described Insolution protocol (Promega). The degraded surfactant was removed by centrifuging the sample at 14,000×g for 15 minutes, and the supernatant transferred to a Total Recovery Vial (Waters) for nLC-MS/MS analysis.

nanoUPLC-MS

The peptide digest was desalted, with an online Symmetry C18 trap column (180 µm×20 mm×5 µm (Waters) at a flow rate of 15 µL/minute with 99% buffer A (0.1% v/v formic acid in water) and 1% buffer B (0.1% v/v formic acid in acetonitrile) for 3 minutes. Peptides were eluted over a 90 minute gradient on a C18 BEH 100 µm×100 µm, 1.7 µm (Waters) column. The nanoAcuity UPLC was coupled to a Synapt G1 (Waters) through a TaperTip emitter (New Objective). Data independent acquisition mode ($MS^E$) in continuum format was used to analyze eluting peptides in the range of 200-3000 m/z. Mass accuracy was maintained using lockspray calibrant ([Glu1]-fibrinopeptide B ([M+2H]$^{2+}$, 785.84206 m/z, Genzyme, Framingham, MA).

Data Analysis $MS^E$ raw data was automatically smoothed, background subtracted, centered, deisotoped, charge state reduced, and mass corrected with Protein Lynx Global Server v2.4 (Waters). Processed data was searched against the human IPI protein database v3.131. Filtering criteria were set to include only proteins with >95% confidence scores. Label free quantitation using Expression Analysis (Waters) was also used to rank order those proteins with a differential expression of >1.5 fold over the control.

Western Blot (Immunoblot) Analysis

Kidney samples were homogenized in RIPA buffer (Boston BioProducts) including 1 mM DTT, 5 mM EDTA, 2 mM NaF, 1 mM $Na_3VO_4$ (all supplied by Sigma-Aldrich), Pefabloc SC and Complete Proteinase Inhibitor Cocktail (both from Roche Applied Science). Protein concentrations were determined by BCA protein assay (Pierce). Urine samples were briefly centrifuged at 3000 RPM for 10 minutes at 4° C. (Beckman Coulter Allegra 6A) to remove cellular debris. An equal volume of urine was diluted in 5× Laemmli Buffer (15% SDS, 0.575 M sucrose, 0.325 M Tris, pH 6.8, 5% beta-mercaptoethanol and 0.002% bromophenol blue). Equal amounts of protein and urine were loaded onto 4-14% NuPage Bis-Tris gels following the manufacturer's protocols (Invitrogen). Membranes were blocked with 5% nonfat milk in Tris-buffered saline (TBS) including 0.1% Tween-20 and incubated with primary antibodies overnight at 4° C. Primary antibodies were detected with horseradish peroxidase-labeled secondary antibodies (Promega). Immunoreactive proteins were detected by enhanced chemiluminescence (GE Healthcare). Primary antibodies to the following proteins were used: α-1-microglobulin and β-actin (Abcam), and GAPDH (US Biological).

Quantitative RT-PCR Analysis

RNA extraction was performed by homogenizing kidneys in TRIzol reagent in the presence of 5 µg glycogen (Invitrogen) following the manufacturer's instructions. Reverse transcriptase reactions were conducted using extracted RNA with the SuperScript III First-Strand Synthesis SuperMix for qRT-PCR following the manufacturer's recommendations (Invitrogen). TaqMan primers were obtained from Applied Biosystems predesigned Taqman Gene Expression assays corresponding to AMBP (Mm00431788_m1). Reactions were performed using TaqMan Gene Expression Master Mix, run on an Applied Biosystems 7500 Real-Time PCR system and normalized to rodent GAPDH expression.

Immunofluorescence

Paraffin-embedded kidney specimens from normal patients and ADPKD patients were obtained from the National Disease Research Institute. Paraffin-embedded kidneys from wild type, jck, control, and Pkd1 cKO were cut in four-micrometer sections and boiled in Antigen Retrieval Solution (DAKO) in a pressure cooker to unmask antigens. The kidney sections were blocked for 1 hour with Protein Block Serum Free (DAKO) overnight at 4° C. Primary antibodies to Lotus tetragonolobus lectin (LTL) (Vector Laboratories) was used at a dilution of 1:1000. Staining was visualized on an Olympus 1×70 microscope with a 20× or 40× objective (Olympus-America). Images were captured with Metamorph Imaging Series software (Molecular Devices Corporation).

Results

Urine from eight human patients with ADPKD (seven female and one male) and three normal human patients. The clinical parameters for each human ADPKD patient are listed in Table 1. Urine for each human subject was collected mid-void from three patients with mild disease (TKV<600 mL) and from five patients with moderately severe ADPKD (TKV>750 mL). Global urinary proteome profiling using LC-MS/MS was used to compare the protein expression in urine from normal controls to each individual ADPKD sample. The data revealed that α-1-microglobulin/bikunin precursor (AMBP) protein was increased in ADPKD patients and that the levels of AMBP protein correlated with total kidney volume (TKV) measurements. A comparison of the AMBP expression from the least diseased (patient 1) and the most diseased (patient 8) ADPKD patients showed a 30-fold difference in AMBP expression, suggesting that AMBP protein levels increased with increasing severity of ADPKD in humans.

Analysis of AMBP Expression in Human ADPKD

The AMBP protein was originally shown to be expressed exclusively in the liver (Salier et al., *Biochem. J.* 296:85-91, 1993; Salier et al., *Biochem. J.* 315:1-9, 1996; Daveau et al., *Biochem. J.* 292:485-492, 1993), but has been shown to be expressed in the kidney (Grewal et al., *Biochem. J.* 387: 609-616, 2005). In the kidney, the expression of the AMBP gene is regulated by an A1M-specific cis elements and transcription factors. There is evidence that in renal tubular cells, there is a lack of cleavage of AMBP protein (Grewal et al., *Biochem. J.* 387:609-616, 2005).

Figure 2:
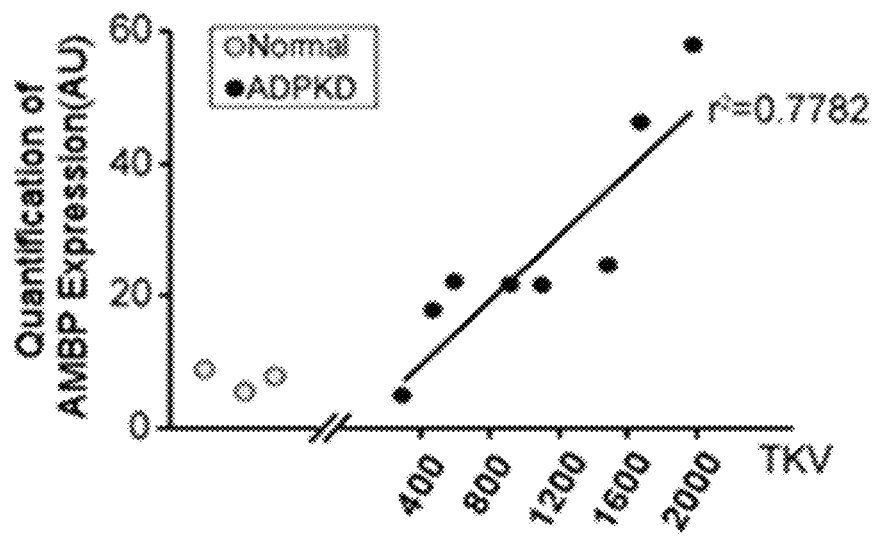
FIG. 2 is a graph showing the quantitated level of AMBP protein in urine in both healthy patients (open circles; normal) and patients having ADPKD (dark circles) (quantitated from the immunoblot of FIG. 1) as a function of total kidney volume (TKV) in the patients.
Figure 3:
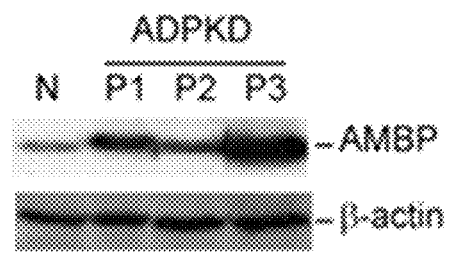
FIG. 3 is an immunoblot showing the level of AMBP protein in kidney lysates from healthy patients (N; normal) and three patients having ADPKD (P1, P2, and P3).
Figure 4:
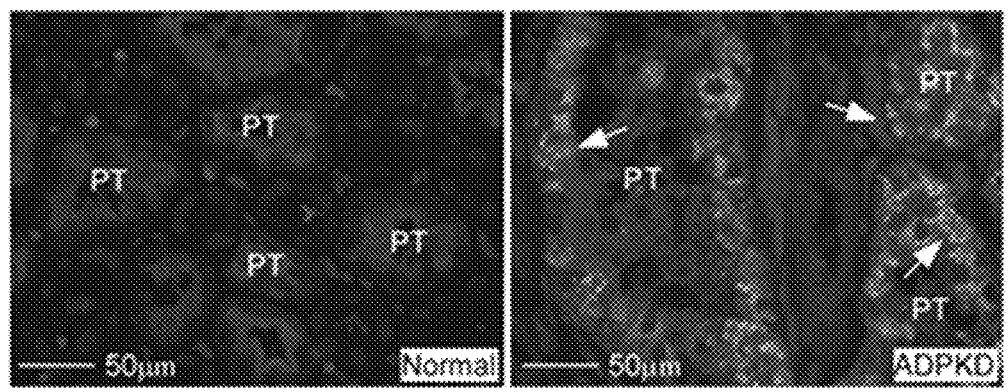
FIG. 4 is an immunofluorescence micrograph of kidney tissue from a healthy (normal patient) (left panel) and a patient having ADPKD (right panel). AMBP protein is shown and localizes to the proximal tubules (PT) (indicated by arrows), lipoprotein lipase (LTL), a marker of PT, and 4',6-diamidino-2-phenylindole (DAPI), a DNA stain, are shown.

Immunoblotting analysis of AMBP protein levels in urine samples from human ADPKD patients was performed to confirm the LC-MS/MS data. The analysis demonstrated that AMBP is up-regulated in urine samples from human ADPKD patients and levels of AMBP expression correlate with disease progression (as indicated by TKV) ($r^2$=0.7782) (FIGS. 1-3). Sections from normal and human ADPKD patient kidneys were stained with a primary antibody against A1M and proximal tubule marker LTL to determine the localization of AMBP expression in human kidneys. As shown in FIG. 4, tubules stained with proximal tubule marker LTL is the site of AMBP protein expression in ADPKD patient kidneys (indicated by arrows), while such expression is not observed in normal patient kidneys. The expression of AMBP protein in ADPKD cystic fluid was confirmed using cyst fluid from three different cysts in a single human ADPKD patient.

These data indicate that AMDP is a marker of PKD.

Assessment of AMBP Expression in the jck Model of PKD

A jck mouse model of PKD (Smith et al., *J. Am. Soc. Nephrol.* 17:2821-2831, 2006) was used to assess the expression of AMBP. Jck mice are characterized by development of moderately progressive renal cystic disease. Kidneys from the jck mouse model are enlarged by day 26 after birth and have multiple cysts. By day 64, little normal tissue remains and there is significantly increased number and size of cysts. Renal function in jck mice, as measured by serum creatinine and blood urea nitrogen, progressively elevates over time. In jck mice, cysts originate early in disease from the collecting ducts and over the progression of cytogenesis, cysts develop from the distal tubules and loop of Henle. Cysts originating from the proximal tubules are not detected in jck mice (Smith et al., *J. Am. Soc. Nephrol.* 17:2821-2831, 2006).

Figure 5:
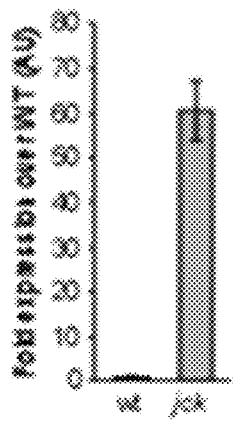
FIG. 5 is a graph showing the fold-expression level of AMBP mRNA in kidneys from a 64-day-old jck mice as compared to wild type (WT) mice. The expression of AMBP mRNA in kidneys from 64-day-old jck mice and WT mice was determined using RT-PCR.
Figure 6:
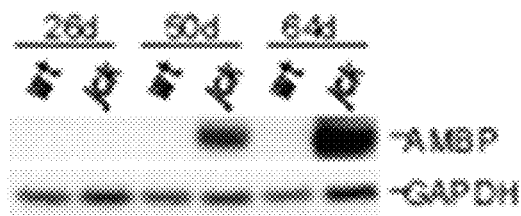
FIG. 6 is an immunoblot showing the level of AMBP protein in kidney lysates from wild type (WT) control mice and jck mice at days 26, 50, and 64 after birth.
Figure 7:
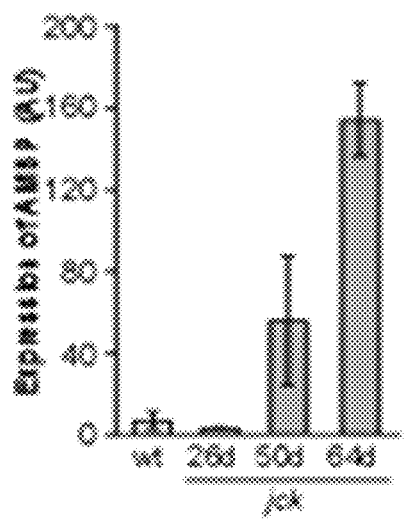
FIG. 7 is a graph showing the quantitated level of AMBP protein in kidney lysates from wild type (WT) control mice and jck mice at days 26, 50, and 64 after birth (quantitated from the immunoblot of FIG. 6).
Figure 8:
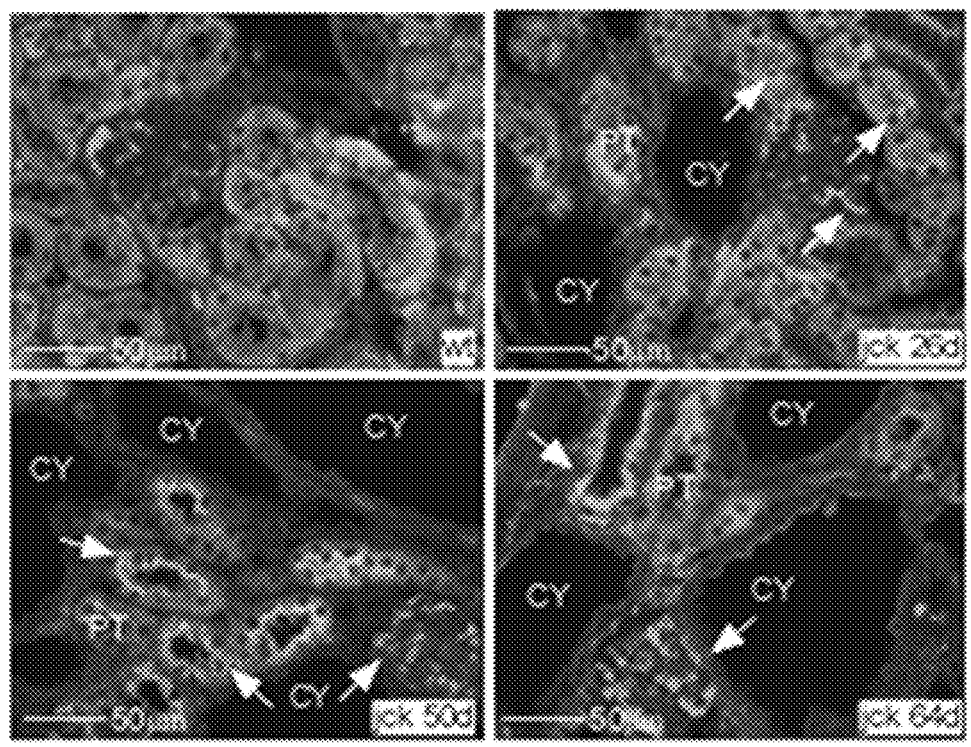
FIG. 8 is an immunofluorescence micrograph of kidney tissue from a wild type control mouse (upper left panel) and a jck mouse at days 26, 50, and 64 after birth (upper right, lower left, and lower right, respectively). AMBP protein, LTL, and DAPI are shown.

The data in FIG. 5 show that, a 64-day-old jck mouse has a 60-fold higher level of AMBP gene expression compared to a wild type mouse control. These data are supported by corresponding immunoblots, which also show a significant elevation of AMBP protein levels in kidneys from 50- and 60-day-old jck mice as compared to wild type mice (FIGS. 6 and 7). Immunofluorescence micrographs of kidney sections from jck mice at 26, 50, and 60 days after birth and wild type mice at 64 days after birth show increasing expression of AMBP protein in proximal tubules and glomeruli over disease progression in jck mice, while little AMBP protein expression is observed in the 64-day old wild type mouse (FIG. 8).

Figure 9:
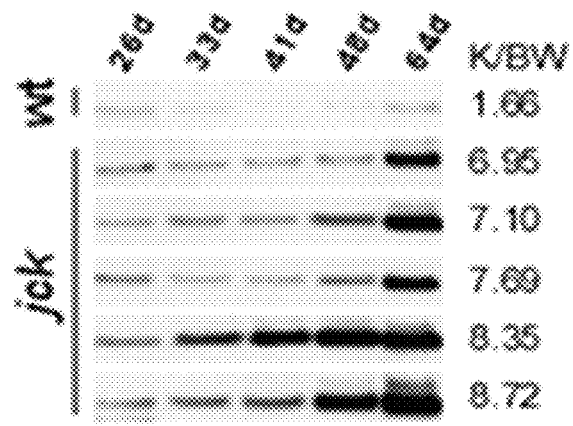
FIG. 9 is an immunoblot showing the level of AMBP protein in urine collected from a wild type mouse and a jck mouse at days 26, day 33, day 41, day 48, and day 64 after birth.
Figure 10:
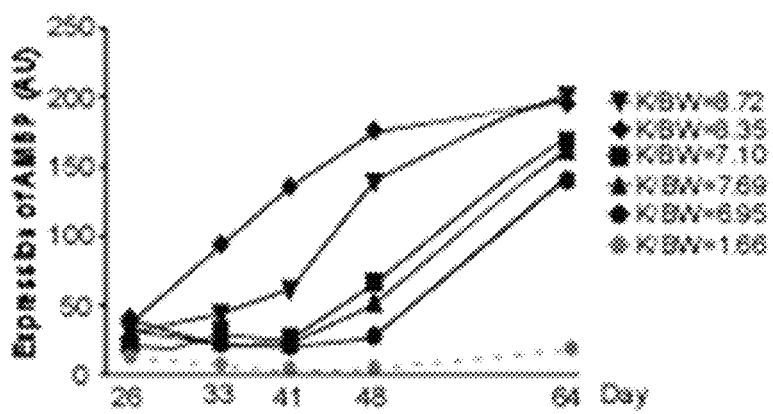
FIG. 10 is a graph showing the quantitated level of AMBP protein in urine collected from a wild type mouse and a jck mouse at day 26, day 33, day 41, day 48, and day 64 after birth (quantitated from the immunoblot of FIG. 9).

In a next set of experiments, AMBP protein levels were measured in urine samples from jck mice at different stages of disease progression. Urine was collected consecutively over a 5-week period from 5 jck mice with a range of disease severity measured by kidney to body weight ratio (final K/BW) at 64 days after birth in the 6.95 to 8.72 range. The immunoblot data show that an elevation in AMBP protein levels occurs starting at day 33 to day 41 after birth and increases progressively in jck mice, and more severe disease is characterized by earlier up-regulation of urinary AMBP protein levels and higher AMBP protein levels at day 64 after birth in jck mice (FIGS. 9 and 10). These data suggest that AMBP protein levels (e.g., urine or kidney tissue AMBP levels) can be used to determine the stage or severity of PKD.

AMBP Expression in an Orthologous Model of ADPKD

Experiments were performed using an Pkd1 cKO (conditional knockout) mouse (Natoli et al., *Nature Med.* 16:788-792, 2010) in order to investigate expression of AMBP in an orthologous mouse model of PKD. In this model, inactivation of Pkd1 on postnatal day 1 results in significant cystogenesis evident by increased kidney to body weight ratio, cyst percentage, and blood urea nitrogen (BUN) (Natoli et al., *Nature Med.* 16:788-792, 2010). The progressive enlargement of cysts in the cortical and medullary regions occurs in two phases, an initial rapid cyst growth (18-26 days of age) followed by a slower growth rate.

Figure 11:
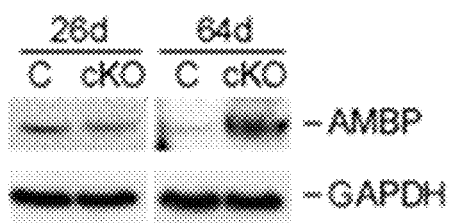
FIG. 11 is an immunoblot showing the levels of AMBP protein in kidney lysates from a wild type (control) mouse and a Pkd1 cKO mouse at day 26 and day 64 after birth.

Immunoblot analysis was used to determine the AMBP protein levels over time in a Pkd1 cKO mouse. The data show AMBP protein levels increase in kidney samples from Pkd1 cKO mice over time (compare the level of expression at day 64 after birth to the level of expression at day 26 after birth) (FIG. 11). Urine was collected consecutively over a 5-week period from Pkd1 mice with a range of disease severity (as measured by cyst percentage) (final Cyst % at 64 days after birth in the 23.3 to 39.6 range) to further investigate urinary levels of AMBP protein in Pkd1 cKO mice.

Figure 12:
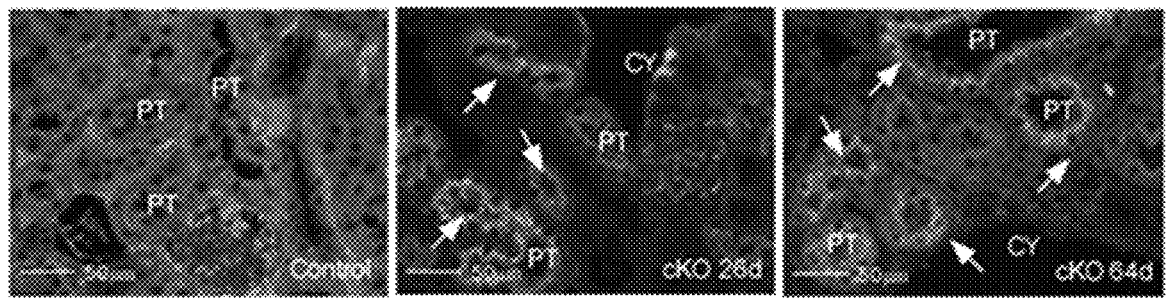
FIG. 12 is an immunofluorescence micrograph of kidney tissue of a wild type (control) mouse (left panel), a Pkd1 cKO mouse at 26 days after birth, and a Pkd1 cKO mouse at 64 days after birth. AMBP protein and LTL are shown, "PT" indicates a proximal tube, and "CY" indicates a cyst.
Figure 13:
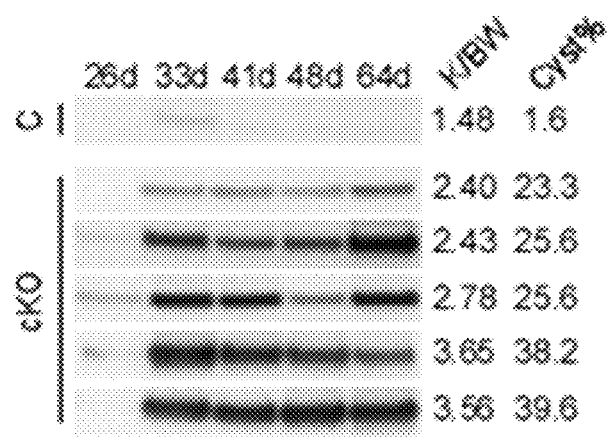
FIG. 13 is an immunoblot showing the level of AMBP protein in urine collected from a wild type (control; C) mouse or a Pkd1 cKO mouse at days 26, 33, 41, 48, and 64 after birth.
Figure 14:
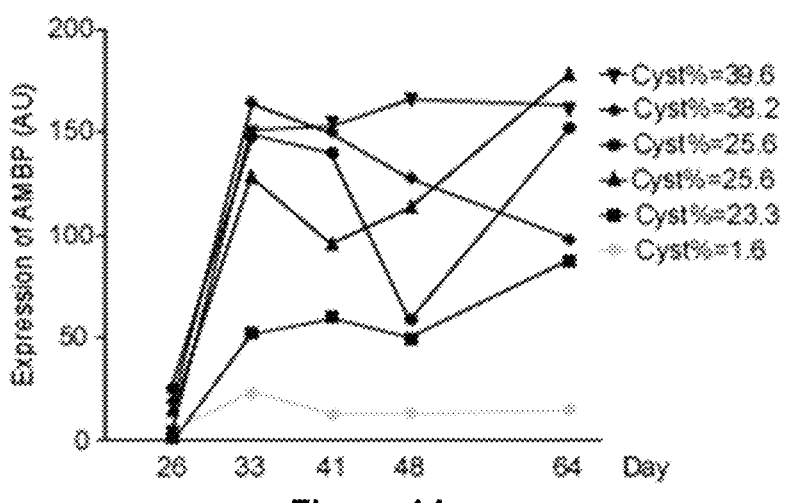
FIG. 14 is a graph showing the quantitated level of AMBP protein in urine collected from control (light data) and three Pkd1 cKO mice at days 26, 33, 41, 48, and 64 after birth (quantitated from the immunoblot of FIG. 13).

The data in FIGS. 13 and 14 show that levels of AMBP protein in urine is increased in Pkd1 mice between 26 to 33 days followed by a relatively slow increase in levels till day 64 after birth (used as a terminal time point for this study). Similar to jck mice kidneys, immunofluorescent analysis of Pkd1 cKO kidney sections showed elevation of AMBP in proximal tubules (FIG. 12).

Example 2. AMBP Expression in Preclinical Models of PKD after Therapeutic Intervention Previously it has been shown that cyclin dependent kinase inhibitors (CDKi) and glucosylceramide synthase inhibitor (GCSi) reduces cystic parameters in mouse models of PKD (Natoli et al., *Nature Med.* 16:788-792, 2010; Bukanov et al., *Nature* 444:949-952, 2006; Bukanov et al., *Cell Cycle* 11:4040-4046, 2012). A set of experiments were performed to determine whether kidney and urinary AMBP expression in jck mice would be reduced after successful therapeutic intervention with CDKi Roscovitine and S-CR8, and a GCSi (Genz-123346).

Materials and Methods

Figure 15:
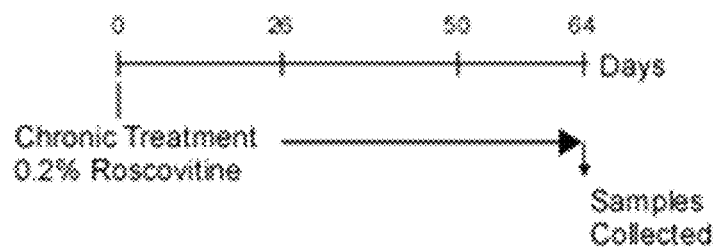
FIG. 15 is a schematic of an animal model study to test the effect of 0.2% roscovitine present in feed on day 26 to day 64 after birth on AMBP protein levels in jck mice.
Figure 16:
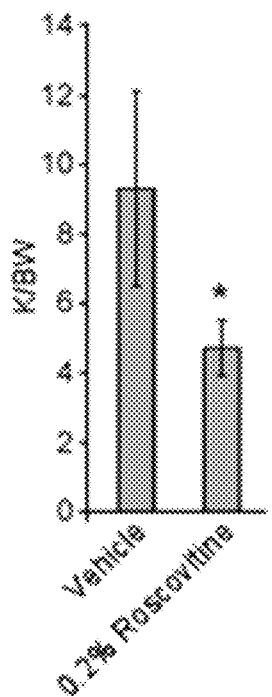
FIG. 16 is a graph showing the kidney to body weight measurements in 64-day-old jck mice which received either vehicle or 0.2% roscovitine in feed on day 26 to day 64 after birth.
Figure 17:
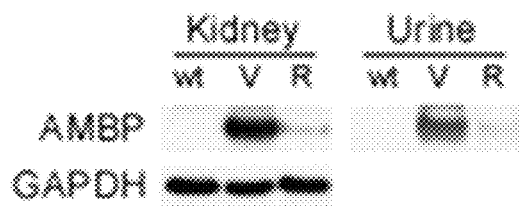
FIG. 17 is a graph showing the level of AMBP protein in kidney lysate and urine of 64-day-old jck mice which received either vehicle or 0.2% roscovitine in feed on day 26 to day 64 after birth.
Figure 18:
FIG. 18 is a schematic of an animal model study to test the effect of different treatment schedules of S-CR8 on cystic volume and AMBP levels in jck mice. Jck mice in the study were treated with one of the following S-CR8 treatment schedules (each starting on day 26 after birth): (A) intraperitoneal injection once a day for 5 weeks; (B) three weeks of daily intraperitoneal injection, and two weeks of no treatment; and (D) one week of daily intraperitoneal injection, and four weeks of no treatment. Urine was collected from all mice at day 64 after birth.

The materials and methods used in this set of experiments is the same as for Example 1, except for the mouse model treatments described below.
Animal Treatments
Roscovitine was administered ad libitum to jck mice from 26 to 64 days of age by mixing in powdered 5053 diet at 0.2%. The GCSi (Genz-123346) was administered ad libitum to jck mice from day 26 to day 64 after birth by mixing in powdered 5053 diet at 0.225% (Natoli et al., *Nature Med.* 16:788-792, 2010). Chronic and pulse treatment with S-CR8 was performed by daily intraperitoneal injection with 24 mg/kg starting from day 26 after birth. The schedules for S-CR8 treatment are shown in FIG. 18. Urine was collected for 24 hours consecutively (at day 26, 33, 41, 48, and 64 after birth) over a 5-week period from animals with a range of disease severity measured by kidney to body weight ratio (K/BW) and cystic percentage (C %).
Results
Treatment with CDK Inhibitors Roscovitine and S-CR8 in Jck Mice
A first set of experiments was performed in jck mice to determine whether administration of roscovitine would decrease both AMBP levels and kidney volume. The data show that oral administration of 0.2% roscovitine between day 26 to day 64 after birth (FIG. 15) results in both a decrease in kidney volume (FIG. 16) and a decrease in AMBP protein levels in both urine and kidney samples from jck mice at day 64 after birth (FIG. 17), as compared to the same parameters measured in a 64-day-old jck mice administered only a vehicle between day 26 to day 64 after birth.

A second set of experiments was performed in jck mice to determine a second CDK inhibitor, S-CR8, would decrease both AMBP levels and kidney volume. In these experiments, the jck animals were administered one of the following treatment schedules starting at day 26 after birth: (A) daily intraperitoneal injection with 24 mg/kg S-CR8 for five weeks; (B) daily intraperitoneal injection with 24 mg/kg S-CR8 for three weeks, and two weeks with no treatment; and (D) daily intraperitoneal injection with 24 mg/kg S-CR8 for one week and four weeks with no treatment (FIG. 18). As a control, jck animals were administered a vehicle between day 26 to day 64 after birth.

Figure 19:
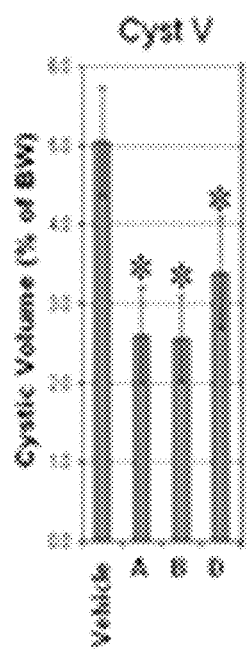
FIG. 19 is a graph showing cystic volume (as a percentage of body weight) in jck mice administered a vehicle daily for five weeks (starting at day 26 after birth) and jck mice administered S-CR8 treatment schedules A, B, and D (as described in FIG. 18).
Figure 20:
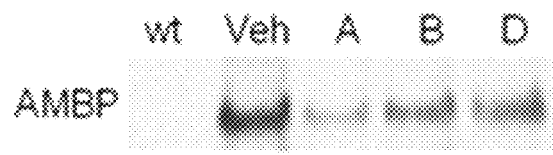
FIG. 20 is an immunoblot showing the level of AMBP protein in urine collected at day 64 after birth in mice administered a vehicle daily for five weeks (starting at day 26 after birth) and jck mice administered S-CR8 treatment schedules A, B, and D (as described in FIG. 18).
Figure 21:
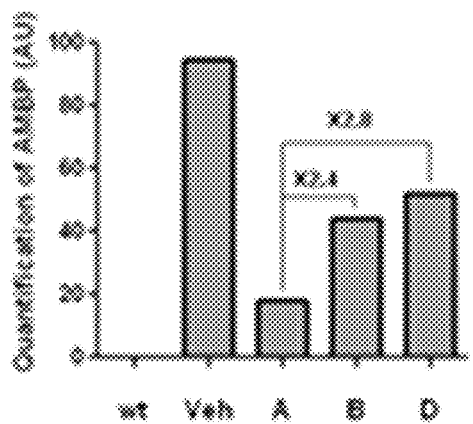
FIG. 21 is a graph showing the quantitated level of AMBP protein in urine collected at day 64 after birth in mice administered a vehicle daily for five weeks (starting at day 26 after birth) and jck mice administered S-CR8 treatment schedules A, B, and D (as described in FIG. 18) (quantitated from the immunoblot of FIG. 20).
Figure 22:
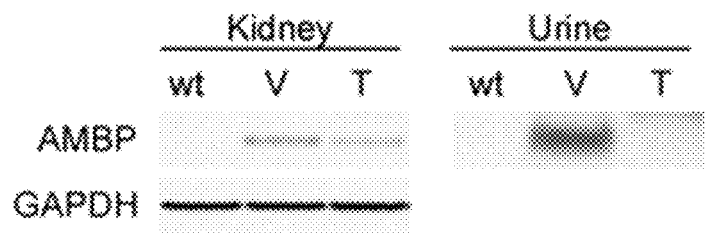
FIG. 22 is an immunoblot showing the level of AMBP protein in urine and kidney lysate obtained from 64-day-old jck mice following chronic treatment between day 26 to day 64 after birth with GCSi.

The data show that daily intraperitoneal injection of 24 mg/kg S-CR8 (in all tested treatment schedules) resulted in a decrease in cyst volume (FIG. 19) and a corresponding decrease in urine AMBP protein levels (FIGS. 20 and 21). These data show that decreasing levels of AMBP can indicate efficacy of a treatment for PKD in a subject.
Treatment with a GCS Inhibitor in Jck Mice
An additional set of experiment was performed to test the effect of administration of a GCS inhibitor, Genz-123346, on AMBP levels in urine and kidney samples of jck mice. The data show that daily administration of 0.225% Genz123346 to jck mice between day 26 to day 64 after birth results in a decrease in both urine and kidney tissue samples at day 64 after birth (FIG. 22) as compared to the corresponding levels in a 64-day-old control jck mouse administered a vehicle between day 26 to day 64 after birth.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining the stage of polycystic kidney disease (PKD) in a patient and treating the patient comprising:
   (a) providing a sample comprising urine from a patient suspected of having PKD or identified as having PKD;
   (b) determining a level of α-1-microglobulin/bikunin precursor (AMBP) protein in the sample;
   (c) determining the stage of PKD in the patient from the level of AMBP protein; and
   (d) administering a glycosyl ceramide synthase (GCS) inhibitor to the patient determined as having stage I, stage II, stage III, stage IV, or stage V PKD, wherein the GCS inhibitor is selected from the group consisting of:
   (S)-quinuclidin-3-yl (2-(4'-(2-methoxyethoxy)-[1,1'-biphenyl]-4-yl)propan-2-yl)carbamate;
   4-fluoro-1-(5-fluoro-4-(4-((2-methoxyethoxy)methyl) phenyl)pyrimidin-2-yl)-N-(4-methyl-1-azabicyclo [3.2.2]nonan-4-yl)piperidine-4-carboxamide;
   4-fluoro-1-(4-(4-((2-methoxyethoxy)methyl)phenyl)pyrimidin-2-yl)-N-(3-methylquinuclidin-3-yl)piperidine-4-carboxamide;
   4-fluoro-1-(4-(4-((2-methoxyethoxy)methyl)phenyl)pyrimidin-2-yl)-N-(4-methyl-1-azabicyclo[3.2.2]nonan-4-yl)piperidine-4-carboxamide;
   4-fluoro-1-(4-(4-(methoxymethyl)phenyl)pyrimidin-2-yl)-N-(3-methylquinuclidin-3-yl) piperidine-4-carboxamide;
   4-fluoro-1-(4-(4-(methoxymethyl)phenyl)pyrimidin-2-yl)-N-(4-methyl-1-azabicyclo[3.2.2]nonan-4-yl)piperidine-4-carboxamide;
   4-fluoro-1-(4-(4-(2-methoxyethoxy)phenyl)pyrimidin-2-yl)-N-(3-methylquinuclidin-3-yl)piperidine-4-carboxamide;
   4-fluoro-1-(4-(4-(2-methoxyethoxy)phenyl)pyrimidin-2-yl)-N-(4-methyl-1-azabicyclo[3.2.2]nonan-4-yl)piperidine-4-carboxamide;
   4-fluoro-1-(4-(4-(2-fluoroethoxy)phenyl)pyrimidin-2-yl)-N-(quinuclidin-3-yl)piperidine-4-carboxamide;
   4-fluoro-1-(4-(4-(2-fluoroethoxy)phenyl)pyrimidin-2-yl)-N-(4-methyl-1-azabicyclo[3.2.2]nonan-4-yl)piperidine-4-carboxamide;
   quinuclidin-3-yl (2-(4'-fluoro-[1,1'-biphenyl]-3-yl)propan-2-yl) carbamate; and
   carbamic acid, N-[1-[2-(4-fluorophenyl)-4-thiazolyl]-1-methylethyl]-, (3S)-1-azabicyclo[2.2.2]oct-3-yl ester, or
   administering hemodialysis or surgical transplantation of a kidney to the patient determined to have stage V PKD.

2. The method of claim 1, further comprising: (e) imaging one or both kidney(s) in the patient after step (c) to confirm the stage of PKD in the patient.

3. The method of claim 1, wherein step (b) comprises contacting the sample with an antibody that binds specifically to AMBP protein.

4. The method of claim 1, wherein the PKD is autosomal dominant PKD.

5. The method of claim 1, wherein the PKD is autosomal recessive PKD.

6. The method of claim 1, wherein the method comprises administering the GCS inhibitor to the patient determined as having stage I, stage II, stage III, stage IV, or stage V PKD.

7. The method of claim 1, wherein the method comprises administering hemodialysis to the patient determined to have stage V PKD.

8. The method of claim 1, wherein the method comprises administering surgical transplantation of a kidney to the patient determined to have stage V PKD.

9. The method of claim 1, wherein the GCS inhibitor is carbamic acid, N-[1-[2-(4-fluorophenyl)-4-thiazolyl]-1-methylethyl]-, (3S)-1-azabicyclo[2.2.2]oct-3-yl ester.

\* \* \* \* \*

SEQUENCE LISTING

```
<160> NUMBER OF SEQ ID NOS: 21

<210> SEQ ID NO 1
<211> LENGTH: 352
<212> TYPE: PRT
<213> ORGANISM: Homo sapiens

<400> SEQUENCE: 1

Met Arg Ser Leu Gly Ala Leu Leu Leu Leu Ser Ala Cys Leu Ala
1               5                   10                  15

Val Ser Ala Gly Pro Val Pro Thr Pro Asp Asn Ile Gln Val Gln
            20                  25                  30

Glu Asn Phe Asn Ile Ser Arg Ile Tyr Gly Lys Trp Tyr Asn Leu Ala
                35                  40                  45

Ile Gly Ser Thr Cys Pro Trp Leu Lys Lys Ile Met Asp Arg Met Thr
        50                  55                  60
```

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp
            115                 120                 125

Glu Tyr Ala Ile Phe Leu Thr Lys Lys Phe Ser Arg His His Gly Pro
130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu
            180                 185                 190

Gln Glu Pro Glu Pro Ile Leu Ile Pro Arg Val Arg Arg Ala Val Leu
            195                 200                 205

Pro Gln Glu Glu Glu Gly Ser Gly Gly Gly Leu Val Thr Glu Val
210                 215                 220

Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255

Glu Thr Phe Gln Tyr Gly Gly Cys Met Gly Asn Gly Asn Asn Phe Val
            260                 265                 270

Thr Glu Lys Glu Cys Leu Gln Thr Cys Arg Thr Val Ala Ala Cys Asn
            275                 280                 285

Leu Pro Ile Val Arg Gly Pro Cys Arg Ala Phe Ile Gln Leu Trp Ala
290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Glu Cys Arg Glu Tyr
                325                 330                 335

Cys Gly Val Pro Gly Asp Gly Asp Glu Glu Leu Leu Arg Phe Ser Asn
            340                 345                 350

<210> SEQ ID NO 2
<211> LENGTH: 333
<212> TYPE: PRT
<213> ORGANISM: Homo sapiens

<400> SEQUENCE: 2

Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
            35                  40                  45

Leu Val Leu Gly Glu Gly Ala Thr Glu Ala Glu Ile Ser Met Thr Ser
50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn

```
                        85                  90                  95
Ile Thr Met Glu Ser Tyr Val Val His Thr Asn Tyr Asp Glu Tyr Ala
                100                 105                 110
Ile Phe Leu Thr Lys Lys Phe Ser Arg His His Gly Pro Thr Ile Thr
                115                 120                 125
Ala Lys Leu Tyr Gly Arg Ala Pro Gln Leu Arg Glu Thr Leu Leu Gln
    130                 135                 140
Asp Phe Arg Val Ala Gln Gly Val Gly Ile Pro Glu Asp Ser Ile
145                 150                 155                 160
Phe Thr Met Ala Asp Arg Gly Glu Cys Val Pro Gly Glu Gln Glu Pro
                165                 170                 175
Glu Pro Ile Leu Ile Pro Arg Val Arg Arg Ala Val Leu Pro Gln Glu
                180                 185                 190
Glu Glu Gly Ser Gly Gly Gln Leu Val Thr Glu Val Thr Lys Lys
                195                 200                 205
Glu Asp Ser Cys Gln Leu Gly Tyr Ser Ala Gly Pro Cys Met Gly Met
    210                 215                 220
Thr Ser Arg Tyr Phe Tyr Asn Gly Thr Ser Met Ala Cys Glu Thr Phe
225                 230                 235                 240
Gln Tyr Gly Gly Cys Met Gly Asn Gly Asn Asn Phe Val Thr Glu Lys
                245                 250                 255
Glu Cys Leu Gln Thr Cys Arg Thr Val Ala Ala Cys Asn Leu Pro Ile
                260                 265                 270
Val Arg Gly Pro Cys Arg Ala Phe Ile Gln Leu Trp Ala Phe Asp Ala
                275                 280                 285
Val Lys Gly Lys Cys Val Leu Phe Pro Tyr Gly Gly Cys Gln Gly Asn
    290                 295                 300
Gly Asn Lys Phe Tyr Ser Glu Lys Glu Cys Arg Glu Tyr Cys Gly Val
305                 310                 315                 320
Pro Gly Asp Gly Asp Glu Glu Leu Leu Arg Phe Ser Asn
                325                 330

<210> SEQ ID NO 3
<211> LENGTH: 184
<212> TYPE: PRT
<213> ORGANISM: Homo sapiens

<400> SEQUENCE: 3

Gly Pro Val Pro Thr Pro Pro Asp Asn Ile Gln Val Gln Glu Asn Phe
1               5                   10                  15
Asn Ile Ser Arg Ile Tyr Gly Lys Trp Tyr Asn Leu Ala Ile Gly Ser
                20                  25                  30
Thr Cys Pro Trp Leu Lys Lys Ile Met Asp Arg Met Thr Val Ser Thr
                35                  40                  45
Leu Val Leu Gly Glu Gly Ala Thr Glu Ala Glu Ile Ser Met Thr Ser
    50                  55                  60
Thr Arg Trp Arg Lys Gly Val Cys Glu Glu Thr Ser Gly Ala Tyr Glu
65              70                  75                  80
Lys Thr Asp Thr Asp Gly Lys Phe Leu Tyr His Lys Ser Lys Trp Asn
                85                  90                  95
Ile Thr Met Glu Ser Tyr Val Val His Thr Asn Tyr Asp Glu Tyr Ala
                100                 105                 110
Ile Phe Leu Thr Lys Lys Phe Ser Arg His His Gly Pro Thr Ile Thr
                115                 120                 125
```

```
Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg Val
                180
```

```
<210> SEQ ID NO 4
<211> LENGTH: 147
<212> TYPE: PRT
<213> ORGANISM: Homo sapiens

<400> SEQUENCE: 4
```

```
Ala Val Leu Pro Gln Glu Glu Gly Ser Gly Gly Gly Gln Leu Val
1               5                   10                  15

Thr Glu Val Thr Lys Lys Glu Asp Ser Cys Gln Leu Gly Tyr Ser Ala
                20                  25                  30

Gly Pro Cys Met Gly Met Thr Ser Arg Tyr Phe Tyr Asn Gly Thr Ser
            35                  40                  45

Met Ala Cys Glu Thr Phe Gln Tyr Gly Gly Cys Met Gly Asn Gly Asn
50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
            115                 120                 125

Arg Glu Tyr Cys Gly Val Pro Gly Asp Gly Asp Glu Glu Leu Leu Arg
130                 135                 140

Phe Ser Asn
145
```

```
<210> SEQ ID NO 5
<211> LENGTH: 69
<212> TYPE: PRT
<213> ORGANISM: Homo sapiens

<400> SEQUENCE: 5
```

```
Val Ala Ala Cys Asn Leu Pro Ile Val Arg Gly Pro Cys Arg Ala Phe
1               5                   10                  15

Ile Gln Leu Trp Ala Phe Asp Ala Val Lys Gly Lys Cys Val Leu Phe
                20                  25                  30

Pro Tyr Gly Gly Cys Gln Gly Asn Gly Asn Lys Phe Tyr Ser Glu Lys
            35                  40                  45

Glu Cys Arg Glu Tyr Cys Gly Val Pro Gly Asp Gly Asp Glu Glu Leu
            50                  55                  60

Leu Arg Phe Ser Asn
65
```

```
<210> SEQ ID NO 6
<211> LENGTH: 261
<212> TYPE: PRT
<213> ORGANISM: Homo sapiens
```

<400> SEQUENCE: 6

Met Phe Glu Ala Arg Leu Val Gln Gly Ser Ile Leu Lys Lys Val Leu
1               5                   10                  15

Glu Ala Leu Lys Asp Leu Ile Asn Glu Ala Cys Trp Asp Ile Ser Ser
            20                  25                  30

Ser Gly Val Asn Leu Gln Ser Met Asp Ser Ser His Val Ser Leu Val
        35                  40                  45

Gln Leu Thr Leu Arg Ser Glu Gly Phe Asp Thr Tyr Arg Cys Asp Arg
    50                  55                  60

Asn Leu Ala Met Gly Val Asn Leu Thr Ser Met Ser Lys Ile Leu Lys
65                  70                  75                  80

Cys Ala Gly Asn Glu Asp Ile Ile Thr Leu Arg Ala Glu Asp Asn Ala
                85                  90                  95

Asp Thr Leu Ala Leu Val Phe Glu Ala Pro Asn Gln Glu Lys Val Ser
            100                 105                 110

Asp Tyr Glu Met Lys Leu Met Asp Leu Asp Val Glu Gln Leu Gly Ile
        115                 120                 125

Pro Glu Gln Glu Tyr Ser Cys Val Val Lys Met Pro Ser Gly Glu Phe
    130                 135                 140

Ala Arg Ile Cys Arg Asp Leu Ser His Ile Gly Asp Ala Val Val Ile
145                 150                 155                 160

Ser Cys Ala Lys Asp Gly Val Lys Phe Ser Ala Ser Gly Glu Leu Gly
                165                 170                 175

Asn Gly Asn Ile Lys Leu Ser Gln Thr Ser Asn Val Asp Lys Glu Glu
            180                 185                 190

Glu Ala Val Thr Ile Glu Met Asn Glu Pro Val Gln Leu Thr Phe Ala
        195                 200                 205

Leu Arg Tyr Leu Asn Phe Phe Thr Lys Ala Thr Pro Leu Ser Ser Thr
    210                 215                 220

Val Thr Leu Ser Met Ser Ala Asp Val Pro Leu Val Val Glu Tyr Lys
225                 230                 235                 240

Ile Ala Asp Met Gly His Leu Lys Tyr Tyr Leu Ala Pro Lys Ile Glu
                245                 250                 255

Asp Glu Glu Gly Ser
            260

<210> SEQ ID NO 7
<211> LENGTH: 295
<212> TYPE: PRT
<213> ORGANISM: Homo sapiens

<400> SEQUENCE: 7

Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Glu Val Phe Pro Leu
65                  70                  75                  80

Ala Met Asn Tyr Leu Asp Arg Phe Leu Ser Leu Glu Pro Val Lys Lys
                85                  90                  95

```
Ser Arg Leu Gln Leu Leu Gly Ala Thr Cys Met Phe Val Ala Ser Lys
                100                 105                 110

Met Lys Glu Thr Ile Pro Leu Thr Ala Glu Lys Leu Cys Ile Tyr Thr
            115                 120                 125

Asp Asn Ser Ile Arg Pro Glu Glu Leu Leu Gln Met Glu Leu Leu Leu
        130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Asn Lys Gln
                165                 170                 175

Ile Ile Arg Lys His Ala Gln Thr Phe Val Ala Leu Cys Ala Thr Asp
                180                 185                 190

Val Lys Phe Ile Ser Asn Pro Pro Ser Met Val Ala Ala Gly Ser Val
            195                 200                 205

Val Ala Ala Val Gln Gly Leu Asn Leu Arg Ser Pro Asn Asn Phe Leu
        210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Val Asp Leu Ala Cys Thr Pro Thr
        275                 280                 285

Asp Val Arg Asp Val Asp Ile
    290                 295

<210> SEQ ID NO 8
<211> LENGTH: 292
<212> TYPE: PRT
<213> ORGANISM: Homo sapiens

<400> SEQUENCE: 8

Met Glu Leu Leu Cys Cys Glu Gly Thr Arg His Ala Pro Arg Ala Gly
1               5                   10                  15

Pro Asp Pro Arg Leu Leu Gly Asp Gln Arg Val Leu Gln Ser Leu Leu
            20                  25                  30

Arg Leu Glu Glu Arg Tyr Val Pro Arg Ala Ser Tyr Phe Gln Cys Val
        35                  40                  45

Gln Arg Glu Ile Lys Pro His Met Arg Lys Met Leu Ala Tyr Trp Met
    50                  55                  60

Leu Glu Val Cys Glu Glu Gln Arg Cys Glu Glu Val Phe Pro Leu
65              70                  75                  80

Ala Met Asn Tyr Leu Asp Arg Tyr Leu Ser Cys Val Pro Thr Arg Lys
                85                  90                  95

Ala Gln Leu Gln Leu Leu Gly Ala Val Cys Met Leu Leu Ala Ser Lys
            100                 105                 110

Leu Arg Glu Thr Thr Pro Leu Thr Ile Glu Lys Leu Cys Ile Tyr Thr
        115                 120                 125

Asp His Ala Val Ser Pro Arg Gln Leu Arg Asp Trp Glu Val Leu Val
    130                 135                 140

Leu Gly Lys Leu Lys Trp Asp Leu Ala Ala Val Ile Ala His Asp Phe
145                 150                 155                 160

Leu Ala Phe Ile Leu His Arg Leu Ser Leu Pro Arg Asp Arg Gln Ala
                165                 170                 175
```

```
Leu Val Lys Lys His Ala Gln Thr Phe Leu Ala Leu Cys Ala Thr Asp
            180                 185                 190

Tyr Thr Phe Ala Met Tyr Pro Pro Ser Met Ile Ala Thr Gly Ser Ile
            195                 200                 205

Gly Ala Ala Val Gln Gly Leu Gly Ala Cys Ser Met Ser Gly Asp Glu
            210                 215                 220

Leu Thr Glu Leu Leu Ala Gly Ile Thr Gly Thr Glu Val Asp Cys Leu
225                 230                 235                 240

Arg Ala Cys Gln Glu Gln Ile Glu Ala Ala Leu Arg Glu Ser Leu Arg
                245                 250                 255

Glu Ala Ser Gln Thr Ser Ser Pro Ala Pro Lys Ala Pro Arg Gly
                260                 265                 270

Ser Ser Ser Gln Gly Pro Ser Gln Thr Ser Thr Pro Thr Asp Val Thr
            275                 280                 285

Ala Ile His Leu
            290

<210> SEQ ID NO 9
<211> LENGTH: 393
<212> TYPE: PRT
<213> ORGANISM: Homo sapiens

<400> SEQUENCE: 9

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
```

```
            245                 250                 255
Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
        290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
                340                 345                 350

Lys Gln Leu Met Val His Ala Phe Ile Lys Arg Ser Asp Ala Glu Glu
                355                 360                 365

Val Asp Phe Ala Gly Trp Leu Cys Ser Thr Ile Gly Leu Asn Gln Pro
        370                 375                 380

Ser Thr Pro Thr His Ala Ala Gly Val
385                 390

<210> SEQ ID NO 10
<211> LENGTH: 367
<212> TYPE: PRT
<213> ORGANISM: Homo sapiens

<400> SEQUENCE: 10

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
                100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Val Ile Lys Gly Leu Thr Tyr Leu Arg Glu Lys His Lys Ile
145                 150                 155                 160

Met His Arg Asp Val Lys Pro Ser Asn Ile Leu Val Asn Ser Arg Gly
                165                 170                 175

Glu Ile Lys Leu Cys Asp Phe Gly Val Ser Gly Gln Leu Ile Asp Ser
                180                 185                 190

Met Ala Asn Ser Phe Val Gly Thr Arg Ser Tyr Met Ser Pro Glu Arg
        195                 200                 205

Leu Gln Gly Thr His Tyr Ser Val Gln Ser Asp Ile Trp Ser Met Gly
    210                 215                 220
```

```
Leu Ser Leu Val Glu Met Ala Val Gly Arg Tyr Pro Ile Pro Pro Pro
225                 230                 235                 240

Asp Ala Lys Glu Leu Glu Leu Met Phe Gly Cys Gln Val Glu Gly Asp
                245                 250                 255

Ala Ala Glu Thr Pro Pro Arg Pro Arg Thr Pro Gly Arg Pro Leu Ser
                260                 265                 270

Ser Tyr Gly Met Asp Ser Arg Pro Met Ala Ile Phe Glu Leu Leu
            275                 280                 285

Asp Tyr Ile Val Asn Glu Pro Pro Lys Leu Pro Ser Gly Val Phe
    290                 295                 300

Ser Leu Glu Phe Gln Asp Phe Val Asn Lys Cys Leu Ile Lys Asn Pro
305                 310                 315                 320

Ala Glu Arg Ala Asp Leu Lys Gln Leu Met Val His Ala Phe Ile Lys
                325                 330                 335

Arg Ser Asp Ala Glu Glu Val Asp Phe Ala Gly Trp Leu Cys Ser Thr
                340                 345                 350

Ile Gly Leu Asn Gln Pro Ser Thr Pro Thr His Ala Ala Gly Val
    355                 360                 365

<210> SEQ ID NO 11
<211> LENGTH: 249
<212> TYPE: PRT
<213> ORGANISM: Homo sapiens

<400> SEQUENCE: 11

Met Lys Leu Asn Ile Ser Phe Pro Ala Thr Gly Cys Gln Lys Leu Ile
1               5                   10                  15

Glu Val Asp Asp Glu Arg Lys Leu Arg Thr Phe Tyr Glu Lys Arg Met
                20                  25                  30

Ala Thr Glu Val Ala Ala Asp Ala Leu Gly Glu Glu Trp Lys Gly Tyr
            35                  40                  45

Val Val Arg Ile Ser Gly Gly Asn Asp Lys Gln Gly Phe Pro Met Lys
    50                  55                  60

Gln Gly Val Leu Thr His Gly Arg Val Arg Leu Leu Leu Ser Lys Gly
65                  70                  75                  80

His Ser Cys Tyr Arg Pro Arg Arg Thr Gly Glu Arg Lys Arg Lys Ser
                85                  90                  95

Val Arg Gly Cys Ile Val Asp Ala Asn Leu Ser Val Leu Asn Leu Val
                100                 105                 110

Ile Val Lys Lys Gly Glu Lys Asp Ile Pro Gly Leu Thr Asp Thr Thr
            115                 120                 125

Val Pro Arg Arg Leu Gly Pro Lys Arg Ala Ser Arg Ile Arg Lys Leu
    130                 135                 140

Phe Asn Leu Ser Lys Glu Asp Asp Val Arg Gln Tyr Val Val Arg Lys
145                 150                 155                 160

Pro Leu Asn Lys Glu Gly Lys Lys Pro Arg Thr Lys Ala Pro Lys Ile
                165                 170                 175

Gln Arg Leu Val Thr Pro Arg Val Leu Gln His Lys Arg Arg Arg Ile
                180                 185                 190

Ala Leu Lys Lys Gln Arg Thr Lys Lys Asn Lys Glu Glu Ala Ala Glu
            195                 200                 205

Tyr Ala Lys Leu Leu Ala Lys Arg Met Lys Glu Ala Lys Glu Lys Arg
    210                 215                 220

Gln Glu Gln Ile Ala Lys Arg Arg Arg Leu Ser Ser Leu Arg Ala Ser
225                 230                 235                 240
```

Thr Ser Lys Ser Glu Ser Ser Gln Lys
            245

<210> SEQ ID NO 12
<211> LENGTH: 379
<212> TYPE: PRT
<213> ORGANISM: Homo sapiens

<400> SEQUENCE: 12

Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
                20                  25                  30

Gly Gln Pro Phe Asp Val Gly Pro Arg Tyr Thr Gln Leu Gln Tyr Ile
            35                  40                  45

Gly Glu Gly Ala Tyr Gly Met Val Ser Ser Ala Tyr Asp His Val Arg
        50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Glu Pro Phe Thr Phe Ala Met Glu Leu
            340                 345                 350

Asp Asp Leu Pro Lys Glu Arg Leu Lys Glu Leu Ile Phe Gln Glu Thr

Ala Arg Phe Gln Pro Gly Val Leu Glu Ala Pro
            370                 375

<210> SEQ ID NO 13
<211> LENGTH: 335
<212> TYPE: PRT
<213> ORGANISM: Homo sapiens

<400> SEQUENCE: 13

Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
            20                  25                  30

Gly Gln Pro Phe Asp Val Gly Pro Arg Tyr Thr Gln Leu Gln Tyr Ile
        35                  40                  45

Gly Glu Gly Ala Tyr Gly Met Val Ser Ser Ala Tyr Asp His Val Arg
    50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
    130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
    210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Ala Leu Asp Leu Leu Asp Arg Met Leu Thr Phe Asn Pro Asn
            260                 265                 270

Lys Arg Ile Thr Val Glu Glu Ala Leu Ala His Pro Tyr Leu Glu Gln
        275                 280                 285

Tyr Tyr Asp Pro Thr Asp Glu Pro Val Ala Glu Pro Phe Thr Phe
    290                 295                 300

Ala Met Glu Leu Asp Asp Leu Pro Lys Glu Arg Leu Lys Glu Leu Ile
305                 310                 315                 320

Phe Gln Glu Thr Ala Arg Phe Gln Pro Gly Val Leu Glu Ala Pro
                325                 330                 335

<210> SEQ ID NO 14
<211> LENGTH: 357

<212> TYPE: PRT
<213> ORGANISM: Homo sapiens

<400> SEQUENCE: 14

Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
            20                  25                  30

Gly Gln Pro Phe Asp Val Gly Pro Arg Tyr Thr Gln Leu Gln Tyr Ile
        35                  40                  45

Gly Glu Gly Ala Tyr Gly Met Val Ser Ser Ala Tyr Asp His Val Arg
    50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
    130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
    210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
    290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Val Gly Gln Ser Pro Ala Ala Val Gly Leu Gly Ala Gly
            340                 345                 350

Glu Gln Gly Gly Thr
        355

<210> SEQ ID NO 15
<211> LENGTH: 360
<212> TYPE: PRT
<213> ORGANISM: Homo sapiens

<400> SEQUENCE: 15

```
Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285

Leu Leu Asp Lys Met Leu Thr Phe Asn Pro His Lys Arg Ile Glu Val
290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
        355                 360
```

<210> SEQ ID NO 16
<211> LENGTH: 316
<212> TYPE: PRT
<213> ORGANISM: Homo sapiens

<400> SEQUENCE: 16

-continued

```
Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
210                 215                 220

Arg Pro Ile Phe Pro Gly Lys His Tyr Leu Asp Gln Leu Asn His Ile
225                 230                 235                 240

Leu Ala Leu Asp Leu Leu Asp Lys Met Leu Thr Phe Asn Pro His Lys
                245                 250                 255

Arg Ile Glu Val Glu Gln Ala Leu Ala His Pro Tyr Leu Glu Gln Tyr
            260                 265                 270

Tyr Asp Pro Ser Asp Glu Pro Ile Ala Glu Ala Pro Phe Lys Phe Asp
        275                 280                 285

Met Glu Leu Asp Asp Leu Pro Lys Glu Lys Leu Lys Glu Leu Ile Phe
290                 295                 300

Glu Glu Thr Ala Arg Phe Gln Pro Gly Tyr Arg Ser
305                 310                 315
```

<210> SEQ ID NO 17
<211> LENGTH: 480
<212> TYPE: PRT
<213> ORGANISM: Homo sapiens

<400> SEQUENCE: 17

```
Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
```

```
                50                  55                  60
Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                 85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
            115                 120                 125

Ser Gly Ala Glu Glu Met Glu Val Ser Leu Ala Lys Pro Lys His Arg
        130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
450                 455                 460

Arg Arg Pro His Phe Pro Gln Phe Ser Tyr Ser Ala Ser Gly Thr Ala
465                 470                 475                 480
```

<210> SEQ ID NO 18
<211> LENGTH: 452
<212> TYPE: PRT
<213> ORGANISM: Homo sapiens

<400> SEQUENCE: 18

```
Met Ala Ala Pro Ser Ala Gly Ser Trp Ser Thr Phe Gln His Lys Glu
1               5                   10                  15

Leu Met Ala Ala Asp Arg Gly Arg Arg Ile Leu Gly Val Cys Gly Met
                20                  25                  30

His Pro His His Gln Glu Thr Leu Lys Lys Asn Arg Val Val Leu Ala
            35                  40                  45

Lys Gln Leu Leu Leu Ser Glu Leu Leu Glu His Leu Leu Glu Lys Asp
        50                  55                  60

Ile Ile Thr Leu Glu Met Arg Glu Leu Ile Gln Ala Lys Val Gly Ser
65                  70                  75                  80

Phe Ser Gln Asn Val Glu Leu Leu Asn Leu Leu Pro Lys Arg Gly Pro
                85                  90                  95

Gln Ala Phe Asp Ala Phe Cys Glu Ala Leu Arg Glu Thr Lys Gln Gly
            100                 105                 110

His Leu Glu Asp Met Leu Leu Thr Thr Leu Ser Gly Leu Gln His Val
        115                 120                 125

Leu Pro Pro Leu Ser Cys Asp Tyr Asp Leu Ser Leu Pro Phe Pro Val
130                 135                 140

Cys Glu Ser Cys Pro Leu Tyr Lys Lys Leu Arg Leu Ser Thr Asp Thr
145                 150                 155                 160

Val Glu His Ser Leu Asp Asn Lys Asp Gly Pro Val Cys Leu Gln Val
                165                 170                 175

Lys Pro Cys Thr Pro Glu Phe Tyr Gln Thr His Phe Gln Leu Ala Tyr
            180                 185                 190

Arg Leu Gln Ser Arg Pro Arg Gly Leu Ala Leu Val Leu Ser Asn Val
        195                 200                 205

His Phe Thr Gly Glu Lys Glu Leu Glu Phe Arg Ser Gly Gly Asp Val
    210                 215                 220

Asp His Ser Thr Leu Val Thr Leu Phe Lys Leu Leu Gly Tyr Asp Val
225                 230                 235                 240

His Val Leu Cys Asp Gln Thr Ala Gln Glu Met Gln Glu Lys Leu Gln
                245                 250                 255

Asn Phe Ala Gln Leu Pro Ala His Arg Val Thr Asp Ser Cys Ile Val
            260                 265                 270

Ala Leu Leu Ser His Gly Val Glu Gly Ala Ile Tyr Gly Val Asp Gly
        275                 280                 285

Lys Leu Leu Gln Leu Gln Glu Val Phe Gln Leu Phe Asp Asn Ala Asn
    290                 295                 300

Cys Pro Ser Leu Gln Asn Lys Pro Lys Met Phe Phe Ile Gln Ala Cys
305                 310                 315                 320

Arg Gly Asp Glu Thr Asp Arg Gly Val Asp Gln Gln Asp Gly Lys Asn
                325                 330                 335

His Ala Gly Ser Pro Gly Cys Glu Glu Ser Asp Ala Gly Lys Glu Lys
            340                 345                 350

Leu Pro Lys Met Arg Leu Pro Thr Arg Ser Asp Met Ile Cys Gly Tyr
        355                 360                 365

Ala Cys Leu Lys Gly Thr Ala Ala Met Arg Asn Thr Lys Arg Gly Ser
```

```
            370                 375                 380
Trp Tyr Ile Glu Ala Leu Ala Gln Val Phe Ser Glu Arg Ala Cys Asp
385                 390                 395                 400

Met His Val Ala Asp Met Leu Val Lys Val Asn Ala Leu Ile Lys Asp
                    405                 410                 415

Arg Glu Gly Tyr Ala Pro Gly Thr Glu Phe His Arg Cys Lys Glu Met
                420                 425                 430

Ser Glu Tyr Cys Ser Thr Leu Cys Arg His Leu Tyr Leu Phe Pro Gly
            435                 440                 445

His Pro Pro Thr
        450

<210> SEQ ID NO 19
<211> LENGTH: 313
<212> TYPE: PRT
<213> ORGANISM: Homo sapiens

<400> SEQUENCE: 19

Met His Pro His His Gln Glu Thr Leu Lys Lys Asn Arg Val Val Leu
1               5                   10                  15

Ala Lys Gln Leu Leu Leu Ser Glu Leu Leu Glu His Leu Leu Glu Lys
            20                  25                  30

Asp Ile Ile Thr Leu Glu Met Arg Glu Leu Ile Gln Ala Lys Val Gly
        35                  40                  45

Ser Phe Ser Gln Asn Val Glu Leu Leu Asn Leu Leu Pro Lys Arg Gly
    50                  55                  60

Pro Gln Ala Phe Asp Ala Phe Cys Glu Ala Leu Arg Glu Thr Lys Gln
65                  70                  75                  80

Gly His Leu Glu Asp Met Leu Leu Thr Thr Leu Ser Gly Leu Gln His
                85                  90                  95

Val Leu Pro Pro Leu Ser Cys Asp Tyr Asp Leu Ser Leu Pro Phe Pro
            100                 105                 110

Val Cys Glu Ser Cys Pro Leu Tyr Lys Lys Leu Arg Leu Ser Thr Asp
        115                 120                 125

Thr Val Glu His Ser Leu Asp Asn Lys Asp Gly Pro Val Cys Leu Gln
    130                 135                 140

Val Lys Pro Cys Thr Pro Glu Phe Tyr Gln Thr His Phe Gln Leu Ala
145                 150                 155                 160

Tyr Arg Leu Gln Ser Arg Pro Arg Gly Leu Ala Leu Val Leu Ser Asn
                165                 170                 175

Val His Phe Thr Gly Glu Lys Glu Leu Glu Phe Arg Ser Gly Gly Asp
            180                 185                 190

Val Asp His Ser Thr Leu Val Thr Leu Phe Lys Leu Leu Gly Tyr Asp
        195                 200                 205

Val His Val Leu Cys Asp Gln Thr Ala Gln Glu Met Gln Glu Lys Leu
    210                 215                 220

Gln Asn Phe Ala Gln Leu Pro Ala His Arg Val Thr Asp Ser Cys Ile
225                 230                 235                 240

Val Ala Leu Leu Ser His Gly Val Glu Gly Ala Ile Tyr Gly Val Asp
                245                 250                 255

Gly Lys Leu Leu Gln Leu Gln Glu Val Phe Gln Leu Phe Asp Asn Ala
            260                 265                 270

Asn Cys Pro Ser Leu Gln Asn Lys Pro Lys Met Phe Phe Ile Gln Ala
        275                 280                 285
```

```
Cys Arg Gly Gly Gly Ala Ile Gly Ser Leu Gly His Leu Leu Leu Phe
    290                 295                 300

Thr Ala Ala Thr Ala Ser Leu Ala Leu
305                 310

<210> SEQ ID NO 20
<211> LENGTH: 91
<212> TYPE: PRT
<213> ORGANISM: Homo sapiens

<400> SEQUENCE: 20

Met Ala Ala Asp Arg Gly Arg Arg Ile Leu Gly Val Cys Gly Met His
1               5                   10                  15

Pro His His Gln Glu Thr Leu Lys Lys Asn Arg Val Val Leu Ala Lys
                20                  25                  30

Gln Leu Leu Leu Ser Glu Leu Leu Glu His Leu Leu Glu Lys Asp Ile
            35                  40                  45

Ile Thr Leu Glu Met Arg Glu Leu Ile Gln Ala Lys Val Gly Ser Phe
50                  55                  60

Ser Gln Asn Val Glu Leu Leu Asn Leu Leu Pro Lys Arg Gly Pro Gln
65                  70                  75                  80

Ala Phe Asp Ala Phe Cys Glu Ala Leu His Ser
                85                  90

<210> SEQ ID NO 21
<211> LENGTH: 425
<212> TYPE: PRT
<213> ORGANISM: Homo sapiens

<400> SEQUENCE: 21

Met Ala Asp Lys Glu Ala Ala Phe Asp Asp Ala Val Glu Glu Arg Val
1               5                   10                  15

Ile Asn Glu Glu Tyr Lys Ile Trp Lys Lys Asn Thr Pro Phe Leu Tyr
                20                  25                  30

Asp Leu Val Met Thr His Ala Leu Glu Trp Pro Ser Leu Thr Ala Gln
            35                  40                  45

Trp Leu Pro Asp Val Thr Arg Pro Glu Gly Lys Asp Phe Ser Ile His
50                  55                  60

Arg Leu Val Leu Gly Thr His Thr Ser Asp Glu Gln Asn His Leu Val
65                  70                  75                  80

Ile Ala Ser Val Gln Leu Pro Asn Asp Asp Ala Gln Phe Asp Ala Ser
                85                  90                  95

His Tyr Asp Ser Glu Lys Gly Glu Phe Gly Gly Phe Gly Ser Val Ser
                100                 105                 110

Gly Lys Ile Glu Ile Glu Ile Lys Ile Asn His Glu Gly Glu Val Asn
            115                 120                 125

Arg Ala Arg Tyr Met Pro Gln Asn Pro Cys Ile Ile Ala Thr Lys Thr
130                 135                 140

Pro Ser Ser Asp Val Leu Val Phe Asp Tyr Thr Lys His Pro Ser Lys
145                 150                 155                 160

Pro Asp Pro Ser Gly Glu Cys Asn Pro Asp Leu Arg Leu Arg Gly His
                165                 170                 175

Gln Lys Glu Gly Tyr Gly Leu Ser Trp Asn Pro Asn Leu Ser Gly His
                180                 185                 190

Leu Leu Ser Ala Ser Asp Asp His Thr Ile Cys Leu Trp Asp Ile Ser
            195                 200                 205
```

-continued

```
Ala Val Pro Lys Glu Gly Lys Val Val Asp Ala Lys Thr Ile Phe Thr
        210             215             220
Gly His Thr Ala Val Glu Asp Val Ser Trp His Leu Leu His Glu
225             230             235             240
Ser Leu Phe Gly Ser Val Ala Asp Asp Gln Lys Leu Met Ile Trp Asp
            245             250             255
Thr Arg Ser Asn Asn Thr Ser Lys Pro Ser His Ser Val Asp Ala His
                260             265             270
Thr Ala Glu Val Asn Cys Leu Ser Phe Asn Pro Tyr Ser Glu Phe Ile
        275             280             285
Leu Ala Thr Gly Ser Ala Asp Lys Thr Val Ala Leu Trp Asp Leu Arg
        290             295             300
Asn Leu Lys Leu Lys Leu His Ser Phe Glu Ser His Lys Asp Glu Ile
305             310             315             320
Phe Gln Val Gln Trp Ser Pro His Asn Glu Thr Ile Leu Ala Ser Ser
            325             330             335
Gly Thr Asp Arg Arg Leu Asn Val Trp Asp Leu Ser Lys Ile Gly Glu
                340             345             350
Glu Gln Ser Pro Glu Asp Ala Glu Asp Gly Pro Pro Glu Leu Leu Phe
            355             360             365
Ile His Gly Gly His Thr Ala Lys Ile Ser Asp Phe Ser Trp Asn Pro
    370             375             380
Asn Glu Pro Trp Val Ile Cys Ser Val Ser Glu Asp Asn Ile Met Gln
385             390             395             400
Val Trp Gln Met Ala Glu Asn Ile Tyr Asn Asp Glu Asp Pro Glu Gly
                405             410             415
Ser Val Asp Pro Glu Gly Gln Gly Ser
            420             425
```